(12) United States Patent
Villagra et al.

(10) Patent No.: US 9,987,258 B2
(45) Date of Patent: Jun. 5, 2018

(54) HISTONE DEACETYLASE AS A MODULATOR OF PDL1 EXPRESSION AND ACTIVITY

(71) Applicant: H. LEE MOFFITT CANCER CENTER AND RESEARCH INSTITUTE, INC., Tampa, FL (US)

(72) Inventors: Alejandro V. Villagra, Tampa, FL (US); Eduardo M. Sotomayor, Tampa, FL (US)

(73) Assignee: H. Lee Moffitt Cancer Center and Research Institute, Inc., Tampa, FL (US)

( * ) Notice: Subject to any disclaimer, the term of this patent is extended or adjusted under 35 U.S.C. 154(b) by 0 days. days.

(21) Appl. No.: 15/120,065

(22) PCT Filed: Apr. 6, 2015

(86) PCT No.: PCT/US2015/024485
§ 371 (c)(1),
(2) Date: Aug. 18, 2016

(87) PCT Pub. No.: WO2015/157162
PCT Pub. Date: Oct. 15, 2015

(65) Prior Publication Data
US 2017/0049755 A1    Feb. 23, 2017

Related U.S. Application Data

(60) Provisional application No. 61/975,858, filed on Apr. 6, 2014, provisional application No. 61/977,003, filed on Apr. 8, 2014.

(51) Int. Cl.
| | | |
|---|---|---|
| *A61K 31/17* | (2006.01) |
| *A61K 31/437* | (2006.01) |
| *A61K 45/06* | (2006.01) |
| *A61K 31/416* | (2006.01) |
| *A61K 31/422* | (2006.01) |
| *A61K 31/505* | (2006.01) |
| *A61K 31/4045* | (2006.01) |
| *A61K 31/4406* | (2006.01) |
| *A61K 31/506* | (2006.01) |

(52) U.S. Cl.
CPC .......... *A61K 31/437* (2013.01); *A61K 31/17* (2013.01); *A61K 31/4045* (2013.01); *A61K 31/416* (2013.01); *A61K 31/422* (2013.01); *A61K 31/4406* (2013.01); *A61K 31/505* (2013.01); *A61K 31/506* (2013.01); *A61K 45/06* (2013.01)

(58) Field of Classification Search
None
See application file for complete search history.

(56) References Cited

U.S. PATENT DOCUMENTS

| | | |
|---|---|---|
| 6,960,648 B2 | 11/2005 | Bonny |
| 8,008,449 B2 | 8/2011 | Korman et al. |
| 8,552,154 B2 | 10/2013 | Freeman et al. |
| 8,617,546 B2 | 12/2013 | Kang et al. |
| 2002/0035243 A1 | 3/2002 | Imfeld et al. |
| 2002/0120100 A1 | 8/2002 | Bonny |
| 2003/0032594 A1 | 2/2003 | Bonny |
| 2012/0270818 A1 | 10/2012 | Marks et al. |

FOREIGN PATENT DOCUMENTS

WO    2007/005874    1/2007

OTHER PUBLICATIONS

Hino R. et al., Tumor Cell Expression of Programmed Cell Death-1 Ligand 1 is a Prognostic Factor for Malignant Melanoma Cancer, Apr. 2010, pp. 1757-1766, abstract.
Hubbert, et al., Nature 471:455-458.
Ihle, Current opinion in cell biology 13:211-217.
International Patent Application No. PCT/US2015/-24485, International Search Report and Written Opinion, dated Jul. 1, 2015.
Jiang, et al., Clin Cancer Res 19:598-609.
Kalin, et al., "Second-Generation Histone Deacetylase 6 Inhibitors Enhance the Immunosuppressive Effects of Foxp3+ T-Reegulatory Cells," J Med Chem 2012, 55(2):639-651.
Korn, et al., Journal of clinical oncology: official journal of the American Society of Clinical Oncology, 26:527-534.
Kortylewski, et al., Cancer Metastasis Rev 24:315-327.
Lee, et al., Proc Natl Acad Sci USA, 109:7765-7769.
Lens, M.B. & Dawes, M. British Journal of Dermatology 150:179-185.
Minucci, S., et al. Nat Rev Cancer 6:38-51 (2006).
Palijan, et al., J Biol Chem 284:30264-30274.
Pardoll, Nat Rev Cancer 12:252-264.
Regis, et al., Seminars in Cell & Development Biology 19:351-359.
Santo, et al., Blood 119:2579-2589.
Serrador, et al., Immunity 20:417-428.
Todd, et al., PLoS Genet 6:e1001240.
Togi, et al., Biochem Biophys Res Commun, 379"616-620.
Topalian, et al., Curr Opin Immunol 24:207-212.
Toropainen, et al., J Mol Biol. 400:284-294.
Valenzuela-Fernandez, et al., Trends in Cell Biology 18:291-297.
Villagra, et al., Oncogene 29:157-173.
Vries, et al., EMBO J 20:6095-6103.
Woan, et al., Immunol Cell Biol 90:55-65.
Wolfle, et al., Eur J Immunol 41:413-424.
Woods, et al., Melanoma Res, 2013; 23(5):341-348.
Yu, et al., Nat Rev Immunol 7:41-51.

(Continued)

Primary Examiner — Heidi Reese
(74) Attorney, Agent, or Firm — Meunier Carlin & Curfman LLC

(57) ABSTRACT

Disclosed herein is a method for modulating Program Death Receptor Ligand 1 (PDL1) in a cancer cell, comprising contacting the cell with a composition comprising a histone deacetylase (HDAC) inhibitor. Also disclosed is a method for treating a tumor in a subject, comprising administering to the subject a therapeutically effective amount of a composition comprising a histone deacetylase (HDAC) inhibitor and a composition comprising a therapeutically effective amount of a Program Death Receptor Ligand 1 (PDL1) inhibitor, a Programmed Death 1 receptor (PD1) inhibitor, or a combination thereof.

5 Claims, 27 Drawing Sheets

(56) References Cited

OTHER PUBLICATIONS

Aldana-Masangkay, et al., J Biomed Biotechnol 2011:875824.
Bots, M., et al., "Rational Combinations Using HDAC Inhibitors," Clinical Cancer Res., 2009, vol. 15, No. 12, pp. 3970-3977; first column-second paragraph, p. 3972 to first column-second paragraph, p. 3973.
Butler et al., "Rational Design and Simple Chemistry Yield a Superior, Neuroprotective HDAC6 Inhibitor, Tubastatin A," J Am Chem Soc, 2010, 132(31):10842-10846.
Francisco, et al., Immunol Rev. 236:219-242.
Glozak, M.A., et al. Gene 363:15-23 (2005).
Govindan, J Biol Chem 285:4489-4510.
Hassel, et al. Br J Cancer, 2010:103, 820-826.

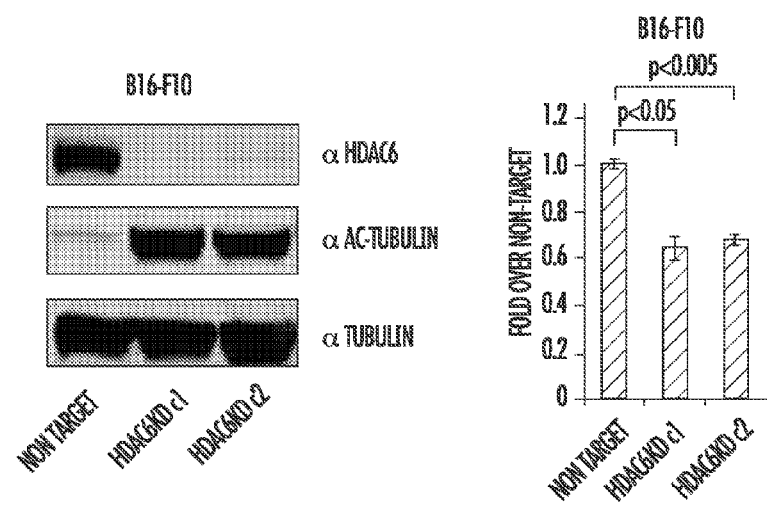
FIG. 10B
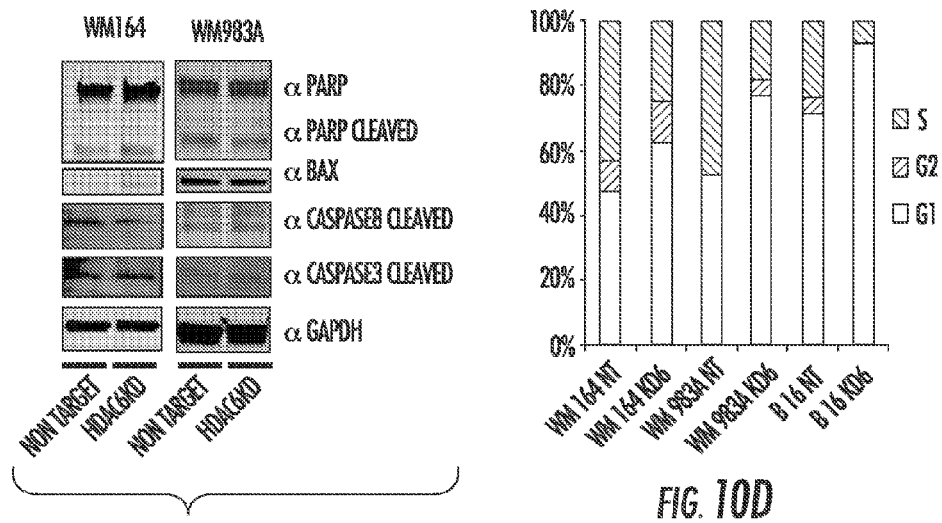
FIG. 10C
FIG. 10D

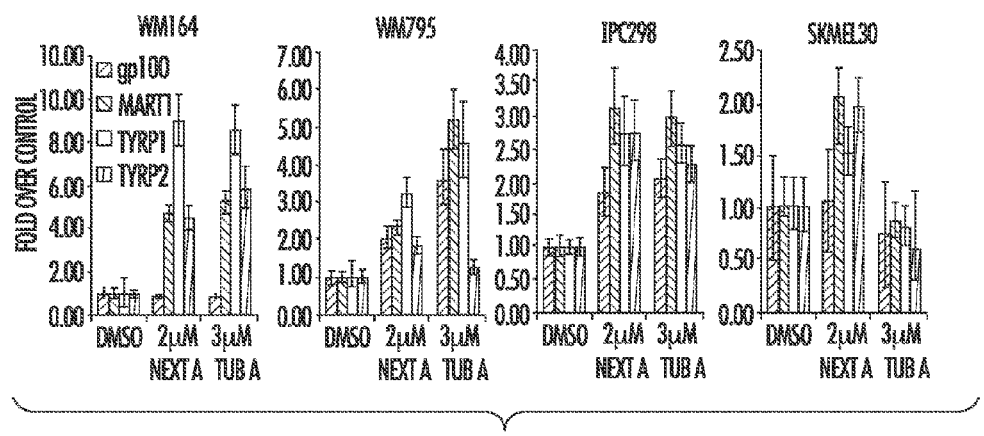
FIG. 11A
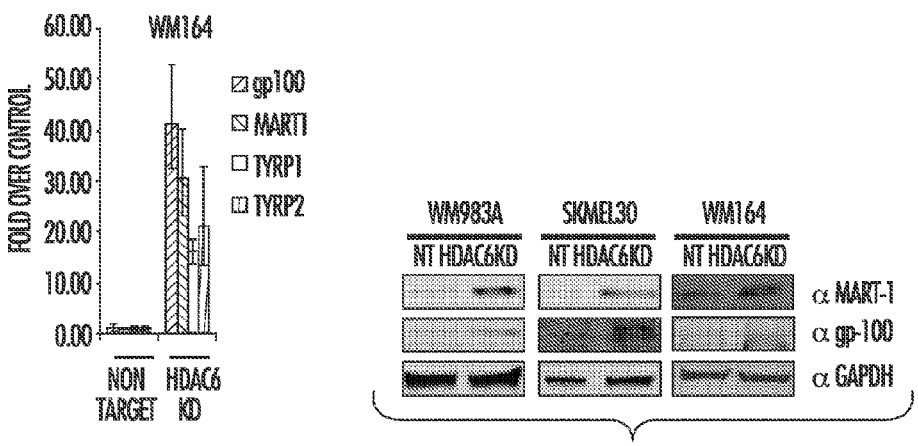
FIG. 11B
FIG. 11C

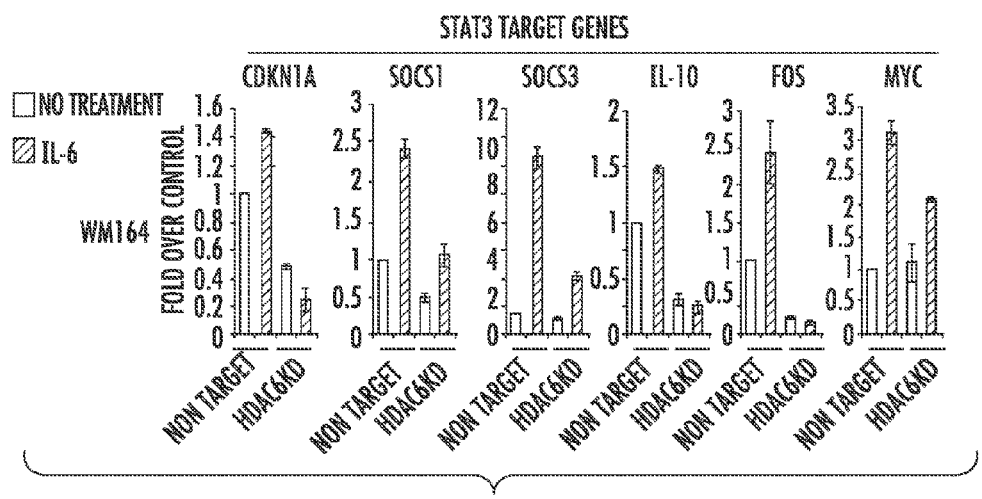
FIG. 16
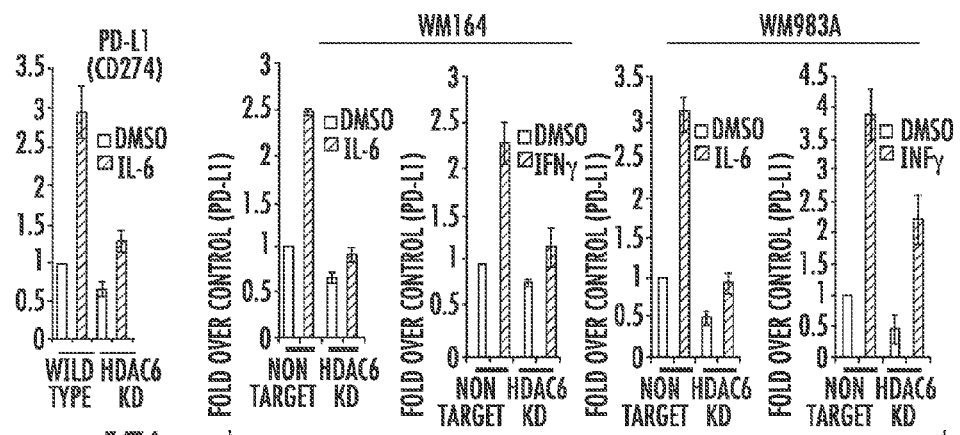
FIG. 17A
FIG. 17B

HISTONE DEACETYLASE AS A MODULATOR OF PDL1 EXPRESSION AND ACTIVITY

CROSS-REFERENCE TO RELATED APPLICATIONS

This application claims benefit of U.S. Provisional Application No. 61/975,858, filed Apr. 6, 2014, and Application Ser. No. 61/977,003, filed Apr. 8, 2014, which are hereby incorporated herein by reference in their entirety.

STATEMENT REGARDING FEDERALLY SPONSORED RESEARCH OR DEVELOPMENT

This invention was made with Government Support under Grant No. CA153246 awarded by the National Institutes of Health. The Government has certain rights in the invention.

BACKGROUND

According to the World Health Organization (WHO), the incidence of melanoma is increasing faster than any other cancer (Lens, M. B. & Dawes, M. British Journal of Dermatology 150:179-185 (2004)). With the advent of new therapies like BRAF inhibitors and ipilimumab, the median overall survival for metastatic melanoma is 11-14 months, and currently there are no other therapies which offer any additional improvement in overall survival (Hassel, J. C., et al. Br J Cancer (2010); Korn, E. L., et al. Journal of clinical oncology: official journal of the American Society of Clinical Oncology 26:527-534 (2008)). There is a high level of interest in defining environmental, genetic and host factors which might be therapeutic targets.

SUMMARY

Histone deacetylases (HDACs), originally described as histone modifiers, have more recently been demonstrated to modify a variety of other proteins involved in diverse cellular processes unrelated to the chromatin environment. This includes deacetylation of multiple non-histone targets, such as proteins involved in cell cycle/apoptosis and immune regulation. This expanded role raises the possibility that the effects of HDACs and HDAC inhibitors (HDACi) may affect non-epigenetic regulatory pathways. In contrast to the well-documented effects of HDACi in the control of cell cycle and apoptosis, their role in immunobiology is still not completely understood, and the reported immunological outcomes when using HDACi are heterogeneous. Disclosed herein is evidence showing that the pharmacological or genetic abrogation of a single HDAC, HDAC6, modifies the immunogenicity and proliferation of melanoma cells. Additionally, HDAC6 interacts with and modulates the activity of STAT3 to control downstream target genes. Among these genes, the Program Death Receptor Ligand 1 (PDL1) is highly susceptible to this regulatory mechanism involving HDAC6 and STAT3. The expression of PDL1 has been shown to be induced in almost every type of cancer, including solid tumors such as melanoma, and it has been proposed that this could be one of the main mechanisms used by cancer cells to acquire resistance to T-cell killing, by activating the negative regulatory pathway PD-1 in T-cells. Thus, this particular regulatory mechanism could be explored to design more efficient and tailored therapies to improve the cancer immune response.

Disclosed herein is a method for modulating Program Death Receptor Ligand 1 (PDL1) in a cancer cell, comprising contacting the cell with a composition comprising a histone deacetylase (HDAC) inhibitor. Also disclosed is a method for treating a tumor in a subject, comprising administering to the subject a therapeutically effective amount of a composition comprising a histone deacetylase (HDAC) inhibitor and a composition comprising a therapeutically effective amount of a Program Death Receptor Ligand 1 (PDL1) inhibitor, a Programmed Death 1 receptor (PD1) inhibitor, or a combination thereof. In some cases, the composition is administered in an amount effective to treat or prevent the cancer cells from becoming resistant to T-cell killing.

In some embodiments, the HDAC inhibitor is a selective inhibitor of histone deacetylase 6 (HDAC6). Selective HDAC6 inhibitors are shown herein to inactivate the STAT3 pathway and down-regulate its target genes, including the expression of PDL1. Non-limiting examples of HDAC6 inhibitors include ACY-1215, Tubacin, Tubastatin A, ST-3-06, ST-2-92, Nexturastat A, and Nexturastat B.

In some embodiments, the HDAC inhibitor is a pan class I HDAC inhibitor. HDAC inhibitors with potency against class I HDACs are shown herein to upregulate the expression of PDL1 in melanoma cell lines. Therefore, in some embodiments, a pan class I HDAC inhibitor can be used when the tumor comprise low PDL1 expression. Non-limiting examples of class I HDAC inhibitors include Vorinostat, LBH589, ITF2357, PXD-101, Depsipeptide, MS-275, and MGCD0103.

In some embodiments, the PDL1 inhibitor comprises an antibody that specifically binds PDL1, such as BMS-936559 (Bristol-Myers Squibb) or MPDL3280A (Roche). In some embodiments, the PD1 inhibitor comprises an antibody that specifically binds PD1, such as lambrolizumab (Merck), nivolumab (Bristol-Myers Squibb), or MEDI4736 (AstraZeneca).

The disclosed composition can be used in combination with other cancer treatments. For example, the disclosed inhibitors of HDAC, PDL1, PD1, or combinations thereof can be administered alone or in combination with a cancer immunotherapy agent. For example, the cancer immunotherapy agent can be an antibody that specifically binds CLTA-4, such as ipilimumab (Bristol-Myers Squibb).

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 1A is a western blot of melanoma cell lines knocked-down for HDAC6 (HDAC6KD). In parallel was evaluated the proliferation of these cells and compared to their homologous non-target (NT) shRNA controls. FIG. 1B is a western blot of HDAC6KD and NT melanoma cells stimulated with IL-6 (30 ng/mL).

FIG. 3A shows the presence of HDAC6, ac-tubulin, and tubulin in melanoma cell lines knocked-down for HDAC6 (HDAC6KD). In parallel was evaluated the proliferation of these cells and compared to their homologous non-target (NT) shRNA controls. FIG. 3B shows the protein expression in HDAC6KD and NT melanoma cells stimulated with IL-6 (30 ng/mL).

FIG. 8 shows that HDAC inhibitors decrease cell proliferation of melanoma cells.

FIG. 9A shows HDAC6 expression in human melanocytes, BRAF mutant, and NRAS mutant melanoma cell lines. FIG. 9B shows HDAC6 expression in 9 primary human melanomas.

FIGS. 10A and 10B show characterization of human (FIG. 10A) and B16 murine (FIG. 10B) HDAC6KD melanoma cell lines. Cell lines were transduced with shRNA either coding for HDAC6 or a non-target sequence. Cells were immunoblotted using specific antibodies to HDAC6, tubulin and acetylated tubulin. Two HDAC6KD clones and two NT controls were analyzed and then subjected to MTS assay. Data is representative of three experiments with similar results. FIG. 10C shows expression of full length and cleaved protein fragments of PARP, BAX, cleaved caspase 8, and cleaved caspase 3 in HDAC6KD and NT melanoma cells. FIG. 10D shows cell cycle analysis of NT and HDAC6KD human melanoma cell lines stained with propidium iodide. Data is representative of three experiments with similar results.

FIGS. 11A to 11C show expression of tumor antigens in Melanoma cell lines. FIG. 11A shows expression of tumor antigens in different melanoma cells incubated with HDAC6i for 48 hours measured by qRT-PCR. FIG. 11B shows expression of tumor antigens measured in WM164 non-target and HDAC6KD cells. FIG. 11C shows expression of tumor antigens measured by western blot.

FIGS. 12A to 1B show increased MHC1 expression after HDAC6 inhibition in melanoma cell lines. FIG. 12A shows MHC I expression in NT and HDAC6KD melanoma cell lines.

FIG. 13 shows HDAC6 modulates tumor growth in vivo.

FIG. 14A shows in vivo growth of B16 WT melanoma injected into SCID mice was not significantly different despite treatment with HDAC6 inhibitor Nexturastat B. FIG. 14B shows in vivo growth of B16 HDAC6KD melanoma cells and control non-target cells in C57BL/6 mice. Mice were treated with antibodies to deplete CD4, CD8, and NK cells. These findings suggest that changes in tumor growth after HDAC6 inhibition are in part, due to the immune recognition of the tumor.

FIG. 15A shows generation of melanoma monoclonal cell lines with or without HDAC6 expression. Melanoma cells were transduced with either shRNA coding for HDAC6 or a non-target sequence. Cells were immunoblotted using specific antibodies to HDAC6, tubulin and acetylated tubulin. FIG. 15B shows phosphorylation of JAK2 and STAT3 measured in different human melanoma NT or HDAC6KD cell lines after stimulation with IL-6. Cells were lysed and immunoblotted using the specific antibodies above.

FIG. 16 shows quantitative RT-PCR of STAT3 target genes. Total RNA was isolated from melanoma cell lines NT and HDAC6KD before and after treatment with IL-6, and the expressions of STAT3 target genes were analyzed by quantitative RT-PCR. The results are expressed as a percent over control cells, and data was normalized by GAPDH expression. This experiment was performed three times with similar results. Error bars represent standard deviation from triplicates.

FIGS. 17A to 17C show PDL-1 expression in melanoma HDAC6KD. FIG. 17A shows PD-L1 expression in HDAC6KO cells versus wild type cells measured by qRT-PC Rafter IL-6 or DMSO. FIG. 17B shows PD-L1 expression in melanoma NT and HDAC6KD cell lines analyzed by qRT-PCR after IL-6 (30 ng/ml), IFN-g (100 ng/ml), or DMSO. FIG. 17C shows PDL1 expression in HDAC6KD cells analyzed by western blot.

FIG. 18A shows STAT3, PDL-1 and GAPDH expression in melanoma monoclonal cell lines with or without STAT3 expression. FIG. 18B shows flow cytometric analysis for PDL-1 in HDACKD, STAT3KD, and non-target melanoma before and after IFN-γ stimulation.

DETAILED DESCRIPTION

Figure 1A:
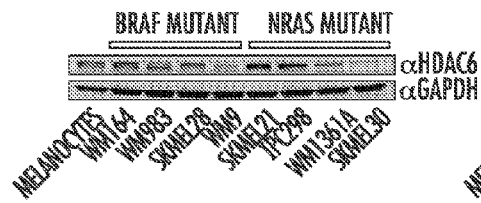
FIGS. 1A and 1B show that HDAC6 knock-down decreases STAT3 activation.

A major challenge to turning on the immune system to attack cancer is that the immune system consists of an elaborate network of checks and balances to avoid over-activation which could harm healthy tissue. For cancer to develop, tumor cells need to hide from the immune systems. One mechanism tumor cells use to hide is exploiting the checks and balances that are in place for down-regulation, by hijacking so called "immune check points" that regulate T-cell activation. Several co-stimulatory pathways have been characterized, including both, activating and inhibiting pathways that determine T-cell activation.

Among several co-stimulatory pathways required for T-cell regulation, the CTLA-4 (cytotoxic T-lymphocyte-associated antigen 4)/B7 inhibitory pathway has been the first target for a pharmaceutical intervention. This pathway is one potential checkpoint that has been hijacked by some tumors to avoid T-cell activation. It predominantly regulates T-cells at the stage of initial T-cell activation. CTLA-4 is expressed within 48 hours after T-cell activation and provides negative signaling that de-activates the T-cell. Inhibition of CTLA-4 by antibodies such as ipilumimab (BMS' Yervoy) or AZN's tremelimumab has resulted in response rate in the 10-15% range in melanoma patients.

Programmed death 1 (PD-1) receptor and PD ligand (PD-L) is another inhibitory pathway that down regulates T-cell activation. PD-1 activities include the inhibition on T-cells during long-term antigen exposure, as happens in chronic viral infections and cancers. T-cell down-regulation is mediated by the interaction of two cell surface molecules (1) PD1 that resides on the T-cell and (2) its ligand PDL1 that sits on the tumor cell. To overcome this down-regulation or T-cell blockade, the PD1/PDL1 interactions needs to be blocked. Such a reversal of the down regulation can be achieved using antibodies, either against the PD1 receptor that blocks the inhibition of the T-cell side or against the ligand PDL1 that blocks the inhibitor on the tumor side.

Histone deacetylases (HDACs) are attractive targets due to the availability of a broad spectrum of inhibitors targeting their enzymatic activity (HDACi). HDACs, originally described as histone modifiers, have recently been demonstrated to modify a variety of other proteins involved in diverse cellular processes unrelated to the chromatin environment. This includes deacetylation of multiple non-histone targets, such as proteins involved in cell cycle/apoptosis and immune regulation (Woan, K. V., et al. Immunol Cell Biol 90:55-65 (2012); Villagra, A., et al. Oncogene 29:157-173 (2010)). This expanded role suggests the possibility that the effects of HDACs and HDACi may include non-epigenetic regulatory pathways.

Selective HDAC6 inhibitors are shown herein to inactivate the STAT3 pathway and down-regulate its target genes, including the expression of PDL1. However, HDAC inhibitors with potency against class I HDACs are shown herein to upregulate the expression of PDL1 in melanoma cell lines. Therefore, in some embodiments, a pan class I HDAC inhibitor can be used when the tumor comprise low PDL1 expression.

A variety of HDAC6 inhibitors have been investigated (Butler et al., "Rational Design and Simple Chemistry Yield a Superior, Neuroprotective HDAC6 Inhibitor, Tubastatin A," *J Am Chem Soc* 2010, 132(31):10842-10846; Kalin et al., "Second-Generation Histone Deacetylase 6 Inhibitors Enhance the Immunosuppressive Effects of Foxp3+ T-Regulatory Cells," *J Med Chem* 2012, 55(2):639-651). Non-limiting examples include ACY-1215, Tubacin, Tubastatin A, ST-3-06, ST-2-92, Nexturastat A, and Nexturastat B.

Non-limiting examples of class I HDAC inhibitors include Vorinostat, LBH589, ITF2357, PXD-101, Depsipeptide, MS-275, and MGCD0103.

The disclosed HDAC inhibitors (pan or specific) can be used alone or in combination with a PD1 or PDL1 inhibitor to treat a tumor in a subject. In some embodiments, the PDL1 inhibitor comprises an antibody that specifically binds PDL1, such as BMS-936559 (Bristol-Myers Squibb) or MPDL3280A (Roche). In some embodiments, the PD1 inhibitor comprises an antibody that specifically binds PD1, such as lambrolizumab (Merck), nivolumab (Bristol-Myers Squibb), or MEDI4736 (AstraZeneca). Human monoclonal antibodies to PD-1 and methods for treating cancer using anti-PD-1 antibodies alone or in combination with other immunotherapeutics are described in U.S. Pat. No. 8,008,449, which is incorporated by reference for these antibodies. Anti-PD-L1 antibodies and uses therefor are described in U.S. Pat. No. 8,552,154, which is incorporated by reference for these antibodies. Anticancer agent comprising anti-PD-1 antibody or anti-PD-L1 antibody are described in U.S. Pat. No. 8,617,546, which is incorporated by reference for these antibodies.

The disclosed compositions and methods can be used in combination with other cancer immunotherapies. There are two distinct types of immunotherapy: passive immunotherapy uses components of the immune system to direct targeted cytotoxic activity against cancer cells, without necessarily initiating an immune response in the patient, while active immunotherapy actively triggers an endogenous immune response. Passive strategies include the use of the monoclonal antibodies (mAbs) produced by B cells in response to a specific antigen. The development of hybridoma technology in the 1970s and the identification of tumor-specific antigens permitted the pharmaceutical development of mAbs that could specifically target tumor cells for destruction by the immune system. Thus far, mAbs have been the biggest success story for immunotherapy; the top three best-selling anticancer drugs in 2012 were mAbs. Among them is rituximab (Rituxan, Genentech), which binds to the CD20 protein that is highly expressed on the surface of B cell malignancies such as non-Hodgkin's lymphoma (NHL). Rituximab is approved by the FDA for the treatment of NHL and chronic lymphocytic leukemia (CLL) in combination with chemotherapy. Another important mAb is trastuzumab (Herceptin; Genentech), which revolutionized the treatment of HER2 (human epidermal growth factor receptor 2)-positive breast cancer by targeting the expression of HER2.

In order to actively drive an antitumor immune response, therapeutic cancer vaccines have been developed. Unlike the prophylactic vaccines that are used preventatively to treat infectious diseases, therapeutic vaccines are designed to treat established cancer by stimulating an immune response against a specific tumor-associated antigen. In 2010, sipuleucel-T (Provenge; Dendreon Corporation) was approved by the FDA for the treatment of metastatic, castration-resistant prostate cancer based on the results of the IMPACT (Immunotherapy Prostate Adenocarcinoma Treatment) trial in which it improved OS by 4.1 months and reduced the risk of death by 22% versus placebo. The advantage of active immunotherapies is that they have the potential to provide long-lasting anticancer activity by engaging both the innate and adaptive arms of the immune response. While mAbs are typically considered passive immunotherapies, there is increasing evidence that they also induce an adaptive immune response via a "vaccination-like" effect.

Generating optimal "killer" CD8 T cell responses also requires T cell receptor activation plus co-stimulation, which can be provided through ligation of tumor necrosis factor receptor family members, including OX40 (CD134) and 4-1BB (CD137). OX40 is of particular interest as treatment with an activating (agonist) anti-OX40 mAb augments T cell differentiation and cytolytic function leading to enhanced anti-tumor immunity against a variety of tumors.

Numerous anti-cancer drugs are available for combination with the present method and compositions. The following is a non-exhaustive lists of anti-cancer (anti-neoplastic) drugs that can be used in conjunction with irradiation: Acivicin; Aclarubicin; Acodazole Hydrochloride; AcrQnine; Adozelesin; Aldesleukin; Altretamine; Ambomycin; Ametantrone Acetate; Aminoglutethimide; Amsacrine; Anastrozole; Anthramycin; Asparaginase; Asperlin; Azacitidine; Azetepa; Azotomycin; Batimastat; Benzodepa; Bicalutamide; Bisantrene Hydrochloride; Bisnafide Dimesylate; Bizelesin; Bleomycin Sulfate; Brequinar Sodium; Bropirimine; Busulfan; Cactinomycin; Calusterone; Caracemide; Carbetimer; Carboplatin; Carmustine; Carubicin Hydrochloride; Carzelesin; Cedefingol; Chlorambucil; Cirolemycin; Cisplatin; Cladribine; Crisnatol Mesylate; Cyclophosphamide; Cytarabine; Dacarbazine; Dactinomycin; Daunorubicin Hydrochloride; Decitabine; Dexormaplatin; Dezaguanine; Dezaguanine Mesylate; Diaziquone; Docetaxel; Doxorubicin; Doxorubicin Hydrochloride; Droloxifene; Droloxifene Citrate; Dromostanolone Propionate; Duazomycin; Edatrexate; Eflornithine Hydrochloride; Elsamitrucin; Enloplatin; Enpromate; Epipropidine; Epirubicin Hydrochloride; Erbulozole; Esorubicin Hydrochloride; Estramustine; Estramustine Phosphate Sodium; Etanidazole; Ethiodized Oil I 131; Etoposide; Etoposide Phosphate; Etoprine; Fadrozole Hydrochloride; Fazarabine; Fenretinide; Floxuridine; Fludarabine Phosphate; Fluorouracil; Flurocitabine; Fosquidone; Fostriecin Sodium; Gemcitabine; Gemcitabine Hydrochloride; Gold Au 198; Hydroxyurea; Idarubicin Hydrochloride; Ifosfamide; Ilmofosine; Iproplatin; Irinotecan Hydrochloride; Lanreotide Acetate; Letrozole; Leuprolide Acetate; Liarozole Hydrochloride; Lometrexol Sodium; Lomustine; Losoxantrone Hydrochloride; Masoprocol; Maytansine; Mechlorethamine Hydrochloride; Megestrol Acetate; Melengestrol Acetate; Melphalan; Menogaril; Mercaptopurine; Methotrexate; Methotrexate Sodium; Metoprine; Meturedepa; Mitindomide; Mitocarcin; Mitocromin; Mitogillin; Mitomalcin; Mitomycin; Mitosper; Mitotane; Mitoxantrone Hydrochloride; Mycophenolic Acid; Nocodazole; Nogalamycin; Ormaplatin; Oxisuran; Paclitaxel; Pegaspargase; Peliomycin; Pentamustine; Peplomycin Sulfate; Perfosfamide; Pipobroman; Piposulfan; Piroxantrone Hydrochloride; Plicamycin; Plomestane; Porfimer Sodium; Porfiromycin; Prednimustine; Procarbazine Hydrochloride; Puromycin; Puromycin Hydrochloride; Pyrazofurin; Riboprine; Rogletimide; Safingol; Safingol Hydrochloride; Semustine; Simtrazene; Sparfosate Sodium; Sparsomycin; Spirogermanium Hydrochloride; Spiromustine; Spiroplatin; Streptonigrin; Streptozocin; Strontium Chloride Sr 89; Sulofenur;

Talisomycin; Taxane; Taxoid; Tecogalan Sodium; Tegafur; Teloxantrone Hydrochloride; Temoporfin; Teniposide; Teroxirone; Testolactone; Thiamiprine; Thioguanine; Thiotepa; Tiazofurin; Tirapazamine; Topotecan Hydrochloride; Toremifene Citrate; Trestolone Acetate; Triciribine Phosphate; Trimetrexate; Trimetrexate Glucuronate; Triptorelin; Tubulozole Hydrochloride; Uracil Mustard; Uredepa; Vapreotide; Verteporfin; Vinblastine Sulfate; Vincristine Sulfate; Vindesine; Vindesine Sulfate; Vinepidine Sulfate; Vinglycinate Sulfate; Vinleurosine Sulfate; Vinorelbine Tartrate; Vinrosidine Sulfate; Vinzolidine Sulfate; Vorozole; Zeniplatin; Zinostatin; Zorubicin Hydrochloride.

The cancer of the disclosed methods can be any cell in a subject undergoing unregulated growth, invasion, or metastasis. In some aspects, the cancer can be any neoplasm or tumor for which radiotherapy is currently used. Alternatively, the cancer can be a neoplasm or tumor that is not sufficiently sensitive to radiotherapy using standard methods. Thus, the cancer can be a sarcoma, lymphoma, leukemia, carcinoma, blastoma, or germ cell tumor. A representative but non-limiting list of cancers that the disclosed compositions can be used to treat include lymphoma, B cell lymphoma, T cell lymphoma, mycosis fungoides, Hodgkin's Disease, myeloid leukemia, bladder cancer, brain cancer, nervous system cancer, head and neck cancer, squamous cell carcinoma of head and neck, kidney cancer, lung cancers such as small cell lung cancer and non-small cell lung cancer, neuroblastoma/glioblastoma, ovarian cancer, pancreatic cancer, prostate cancer, skin cancer, liver cancer, melanoma, squamous cell carcinomas of the mouth, throat, larynx, and lung, colon cancer, cervical cancer, cervical carcinoma, breast cancer, epithelial cancer, renal cancer, genitourinary cancer, pulmonary cancer, esophageal carcinoma, head and neck carcinoma, large bowel cancer, hematopoietic cancers; testicular cancer; colon and rectal cancers, prostatic cancer, and pancreatic cancer.

Compositions, Formulations and Methods of Administration

In vivo application of the disclosed compounds, and compositions containing them, can be accomplished by any suitable method and technique presently or prospectively known to those skilled in the art. For example, the disclosed compounds can be formulated in a physiologically- or pharmaceutically-acceptable form and administered by any suitable route known in the art including, for example, oral, nasal, rectal, topical, and parenteral routes of administration. As used herein, the term parenteral includes subcutaneous, intradermal, intravenous, intramuscular, intraperitoneal, and intrasternal administration, such as by injection. Administration of the disclosed compounds or compositions can be a single administration, or at continuous or distinct intervals as can be readily determined by a person skilled in the art.

The compounds disclosed herein, and compositions comprising them, can also be administered utilizing liposome technology, slow release capsules, implantable pumps, and biodegradable containers. These delivery methods can, advantageously, provide a uniform dosage over an extended period of time. The compounds can also be administered in their salt derivative forms or crystalline forms.

The compounds disclosed herein can be formulated according to known methods for preparing pharmaceutically acceptable compositions. Formulations are described in detail in a number of sources which are well known and readily available to those skilled in the art. For example, Remington's Pharmaceutical Science by E. W. Martin (1995) describes formulations that can be used in connection with the disclosed methods. In general, the compounds disclosed herein can be formulated such that an effective amount of the compound is combined with a suitable carrier in order to facilitate effective administration of the compound. The compositions used can also be in a variety of forms. These include, for example, solid, semi-solid, and liquid dosage forms, such as tablets, pills, powders, liquid solutions or suspension, suppositories, injectable and infusible solutions, and sprays. The preferred form depends on the intended mode of administration and therapeutic application. The compositions also preferably include conventional pharmaceutically-acceptable carriers and diluents which are known to those skilled in the art. Examples of carriers or diluents for use with the compounds include ethanol, dimethyl sulfoxide, glycerol, alumina, starch, saline, and equivalent carriers and diluents. To provide for the administration of such dosages for the desired therapeutic treatment, compositions disclosed herein can advantageously comprise between about 0.1% and 99%, and especially, 1 and 15% by weight of the total of one or more of the subject compounds based on the weight of the total composition including carrier or diluent.

Formulations suitable for administration include, for example, aqueous sterile injection solutions, which can contain antioxidants, buffers, bacteriostats, and solutes that render the formulation isotonic with the blood of the intended recipient; and aqueous and nonaqueous sterile suspensions, which can include suspending agents and thickening agents. The formulations can be presented in unit-dose or multi-dose containers, for example sealed ampoules and vials, and can be stored in a freeze dried (lyophilized) condition requiring only the condition of the sterile liquid carrier, for example, water for injections, prior to use. Extemporaneous injection solutions and suspensions can be prepared from sterile powder, granules, tablets, etc. It should be understood that in addition to the ingredients particularly mentioned above, the compositions disclosed herein can include other agents conventional in the art having regard to the type of formulation in question.

Compounds disclosed herein, and compositions comprising them, can be delivered to a cell either through direct contact with the cell or via a carrier means. Carrier means for delivering compounds and compositions to cells are known in the art and include, for example, encapsulating the composition in a liposome moiety. Another means for delivery of compounds and compositions disclosed herein to a cell comprises attaching the compounds to a protein or nucleic acid that is targeted for delivery to the target cell. U.S. Pat. No. 6,960,648 and U.S. Application Publication Nos. 20030032594 and 20020120100 disclose amino acid sequences that can be coupled to another composition and that allows the composition to be translocated across biological membranes. U.S. Application Publiation No. 20020035243 also describes compositions for transporting biological moieties across cell membranes for intracellular delivery. Compounds can also be incorporated into polymers, examples of which include poly (D-L lactide-co-glycolide) polymer for intracranial tumors; poly[bis(p-carboxyphenoxy) propane:sebacic acid] in a 20:80 molar ratio (as used in GLIADEL); chondroitin; chitin; and chitosan.

For the treatment of oncological disorders, the compounds disclosed herein can be administered to a patient in need of treatment in combination with other antitumor or anticancer substances and/or with radiation and/or photodynamic therapy and/or with surgical treatment to remove a tumor. These other substances or treatments can be given at the same as or at different times from the compounds disclosed herein. For example, the compounds disclosed herein can be used in combination with mitotic inhibitors such as taxol or vinblastine, alkylating agents such as cyclophosamide or ifosfamide, antimetabolites such as 5-fluorouracil or hydroxyurea, DNA intercalators such as adriamycin or bleomycin, topoisomerase inhibitors such as etoposide or camptothecin, antiangiogenic agents such as angiostatin, antiestrogens such as tamoxifen, and/or other anti-cancer drugs or antibodies, such as, for example, GLEEVEC (Novartis Pharmaceuticals Corporation) and HERCEPTIN (Genentech, Inc.), respectively, or an immunotherapeutic such as ipilimumab and bortezomib.

In certain examples, compounds and compositions disclosed herein can be locally administered at one or more anatomical sites, such as sites of unwanted cell growth (such as a tumor site or benign skin growth, e.g., injected or topically applied to the tumor or skin growth), optionally in combination with a pharmaceutically acceptable carrier such as an inert diluent. Compounds and compositions disclosed herein can be systemically administered, such as intravenously or orally, optionally in combination with a pharmaceutically acceptable carrier such as an inert diluent, or an assimilable edible carrier for oral delivery. They can be enclosed in hard or soft shell gelatin capsules, can be compressed into tablets, or can be incorporated directly with the food of the patient's diet. For oral therapeutic administration, the active compound can be combined with one or more excipients and used in the form of ingestible tablets, buccal tablets, troches, capsules, elixirs, suspensions, syrups, wafers, aerosol sprays, and the like.

The tablets, troches, pills, capsules, and the like can also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring can be added. When the unit dosage form is a capsule, it can contain, in addition to materials of the above type, a liquid carrier, such as a vegetable oil or a polyethylene glycol. Various other materials can be present as coatings or to otherwise modify the physical form of the solid unit dosage form. For instance, tablets, pills, or capsules can be coated with gelatin, wax, shellac, or sugar and the like. A syrup or elixir can contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound can be incorporated into sustained-release preparations and devices.

Compounds and compositions disclosed herein, including pharmaceutically acceptable salts, or hydrates thereof, can be administered intravenously, intramuscularly, or intraperitoneally by infusion or injection. Solutions of the active agent or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations can contain a preservative to prevent the growth of microorganisms.

The pharmaceutical dosage forms suitable for injection or infusion can include sterile aqueous solutions or dispersions or sterile powders comprising the active ingredient, which are adapted for the extemporaneous preparation of sterile injectable or infusible solutions or dispersions, optionally encapsulated in liposomes. The ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. Optionally, the prevention of the action of microorganisms can be brought about by various other antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the inclusion of agents that delay absorption, for example, aluminum monostearate and gelatin.

Sterile injectable solutions are prepared by incorporating a compound and/or agent disclosed herein in the required amount in the appropriate solvent with various other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, compounds and agents disclosed herein can be applied in as a liquid or solid. However, it will generally be desirable to administer them topically to the skin as compositions, in combination with a dermatologically acceptable carrier, which can be a solid or a liquid. Compounds and agents and compositions disclosed herein can be applied topically to a subject's skin to reduce the size (and can include complete removal) of malignant or benign growths, or to treat an infection site. Compounds and agents disclosed herein can be applied directly to the growth or infection site. Preferably, the compounds and agents are applied to the growth or infection site in a formulation such as an ointment, cream, lotion, solution, tincture, or the like.

Useful solid carriers include finely divided solids such as talc, clay, microcrystalline cellulose, silica, alumina and the like. Useful liquid carriers include water, alcohols or glycols or water-alcohol/glycol blends, in which the compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers, for example.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Useful dosages of the compounds and agents and pharmaceutical compositions disclosed herein can be determined by comparing their in vitro activity, and in vivo activity in animal models. Methods for the extrapolation of effective dosages in mice, and other animals, to humans are known to the art.

Also disclosed are pharmaceutical compositions that comprise a compound disclosed herein in combination with a pharmaceutically acceptable carrier. Pharmaceutical compositions adapted for oral, topical or parenteral administration, comprising an amount of a compound constitute a preferred aspect. The dose administered to a patient, particularly a human, should be sufficient to achieve a therapeutic response in the patient over a reasonable time frame, without lethal toxicity, and preferably causing no more than an acceptable level of side effects or morbidity. One skilled in the art will recognize that dosage will depend upon a variety of factors including the condition (health) of the subject, the body weight of the subject, kind of concurrent treatment, if any, frequency of treatment, therapeutic ratio, as well as the severity and stage of the pathological condition.

Definitions

The term "subject" refers to any individual who is the target of administration or treatment. The subject can be a vertebrate, for example, a mammal. Thus, the subject can be a human or veterinary patient. The term "patient" refers to a subject under the treatment of a clinician, e.g., physician.

The term "therapeutically effective" refers to the amount of the composition used is of sufficient quantity to ameliorate one or more causes or symptoms of a disease or disorder. Such amelioration only requires a reduction or alteration, not necessarily elimination.

The term "treatment" refers to the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder.

The term "prevent" refers to a treatment that forestalls or slows the onset of a disease or condition or reduced the severity of the disease or condition. Thus, if a treatment can treat a disease in a subject having symptoms of the disease, it can also prevent that disease in a subject who has yet to suffer some or all of the symptoms.

The term "inhibit" refers to a decrease in an activity, response, condition, disease, or other biological parameter. This can include but is not limited to the complete ablation of the activity, response, condition, or disease. This may also include, for example, a 10% reduction in the activity, response, condition, or disease as compared to the native or control level. Thus, the reduction can be a 10, 20, 30, 40, 50, 60, 70, 80, 90, 100%, or any amount of reduction in between as compared to native or control levels.

The term "antibody" refers to natural or synthetic antibodies that selectively bind a target antigen. The term includes polyclonal and monoclonal antibodies. In addition to intact immunoglobulin molecules, also included in the term "antibodies" are fragments or polymers of those immunoglobulin molecules, and human or humanized versions of immunoglobulin molecules that selectively bind the target antigen.

Antibodies that can be used in the disclosed compositions and methods include whole immunoglobulin (i.e., an intact antibody) of any class, fragments thereof, and synthetic proteins containing at least the antigen binding variable domain of an antibody. The variable domains differ in sequence among antibodies and are used in the binding and specificity of each particular antibody for its particular antigen. However, the variability is not usually evenly distributed through the variable domains of antibodies. It is typically concentrated in three segments called complementarity determining regions (CDRs) or hypervariable regions both in the light chain and the heavy chain variable domains. The more highly conserved portions of the variable domains are called the framework (FR). The variable domains of native heavy and light chains each comprise four FR regions, largely adopting a beta-sheet configuration, connected by three CDRs, which form loops connecting, and in some cases forming part of, the beta-sheet structure. The CDRs in each chain are held together in close proximity by the FR regions and, with the CDRs from the other chain, contribute to the formation of the antigen binding site of antibodies.

Also disclosed are fragments of antibodies which have bioactivity. The fragments, whether attached to other sequences or not, include insertions, deletions, substitutions, or other selected modifications of particular regions or specific amino acids residues, provided the activity of the fragment is not significantly altered or impaired compared to the nonmodified antibody or antibody fragment.

Techniques can also be adapted for the production of single-chain antibodies specific to an antigenic protein of the present disclosure. Methods for the production of single-chain antibodies are well known to those of skill in the art. A single chain antibody can be created by fusing together the variable domains of the heavy and light chains using a short peptide linker, thereby reconstituting an antigen binding site on a single molecule. Single-chain antibody variable fragments (scFvs) in which the C-terminus of one variable domain is tethered to the N-terminus of the other variable domain via a 15 to 25 amino acid peptide or linker have been developed without significantly disrupting antigen binding or specificity of the binding. The linker is chosen to permit the heavy chain and light chain to bind together in their proper conformational orientation.

Divalent single-chain variable fragments (di-scFvs) can be engineered by linking two scFvs. This can be done by producing a single peptide chain with two VH and two VL regions, yielding tandem scFvs. ScFvs can also be designed with linker peptides that are too short for the two variable regions to fold together (about five amino acids), forcing scFvs to dimerize. This type is known as diabodies. Diabodies have been shown to have dissociation constants up to 40-fold lower than corresponding scFvs, meaning that they have a much higher affinity to their target. Still shorter linkers (one or two amino acids) lead to the formation of trimers (triabodies or tribodies). Tetrabodies have also been produced. They exhibit an even higher affinity to their targets than diabodies.

The term "monoclonal antibody" as used herein refers to an antibody obtained from a substantially homogeneous population of antibodies, i.e., the individual antibodies within the population are identical except for possible naturally occurring mutations that may be present in a small subset of the antibody molecules. The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, as long as they exhibit the desired antagonistic activity.

The term "specifically binds", as used herein, when referring to a polypeptide (including antibodies) or receptor, refers to a binding reaction which is determinative of the presence of the protein or polypeptide or receptor in a heterogeneous population of proteins and other biologics. Thus, under designated conditions (e g immunoassay conditions in the case of an antibody), a specified ligand or antibody "specifically binds" to its particular "target" (e.g. an antibody specifically binds to an endothelial antigen) when it does not bind in a significant amount to other proteins present in the sample or to other proteins to which the ligand or antibody may come in contact in an organism. Generally, a first molecule that "specifically binds" a second molecule has an affinity constant (Ka) greater than about $10^5$ $M^{-1}$ (e.g., $10^6$ $M^{-1}$, $10^7$ $M^{-1}$, $10^8$ $M^{-1}$, $10^9$ $M^{-1}$, $10^{10}$ $M^{-1}$, $10^{11}$ $M^{-1}$, and $10^{12}$ $M^{-1}$ or more) with that second molecule.

The term "cancer" or "malignant neoplasm" refers to a cell that displays uncontrolled growth, invasion upon adjacent tissues, and often metastasis to other locations of the body.

A number of embodiments of the invention have been described. Nevertheless, it will be understood that various modifications may be made without departing from the spirit and scope of the invention. Accordingly, other embodiments are within the scope of the following claims.

EXAMPLES

Example 1: HDAC6 as a Modulator of PDL1 Expression and Activity

Results

Figure 1B:
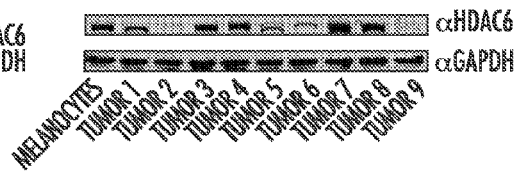
Figure 2A:
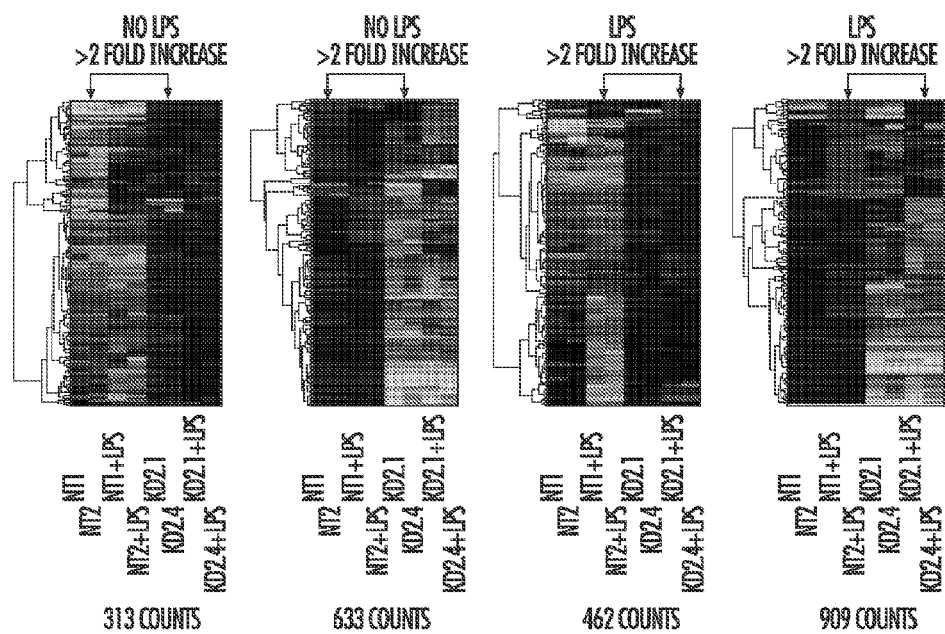
FIG. 2A is a Heat Map of the gene expression profiles obtained by microarray. Genes were clustered according to their properties using the software GeneCluster 3.0. The values for gene expression obtained from two clones for each cell line and compared with their respective controls. Shown are the genes with an over two-fold increase or decrease in both clones.
Figure 2B:
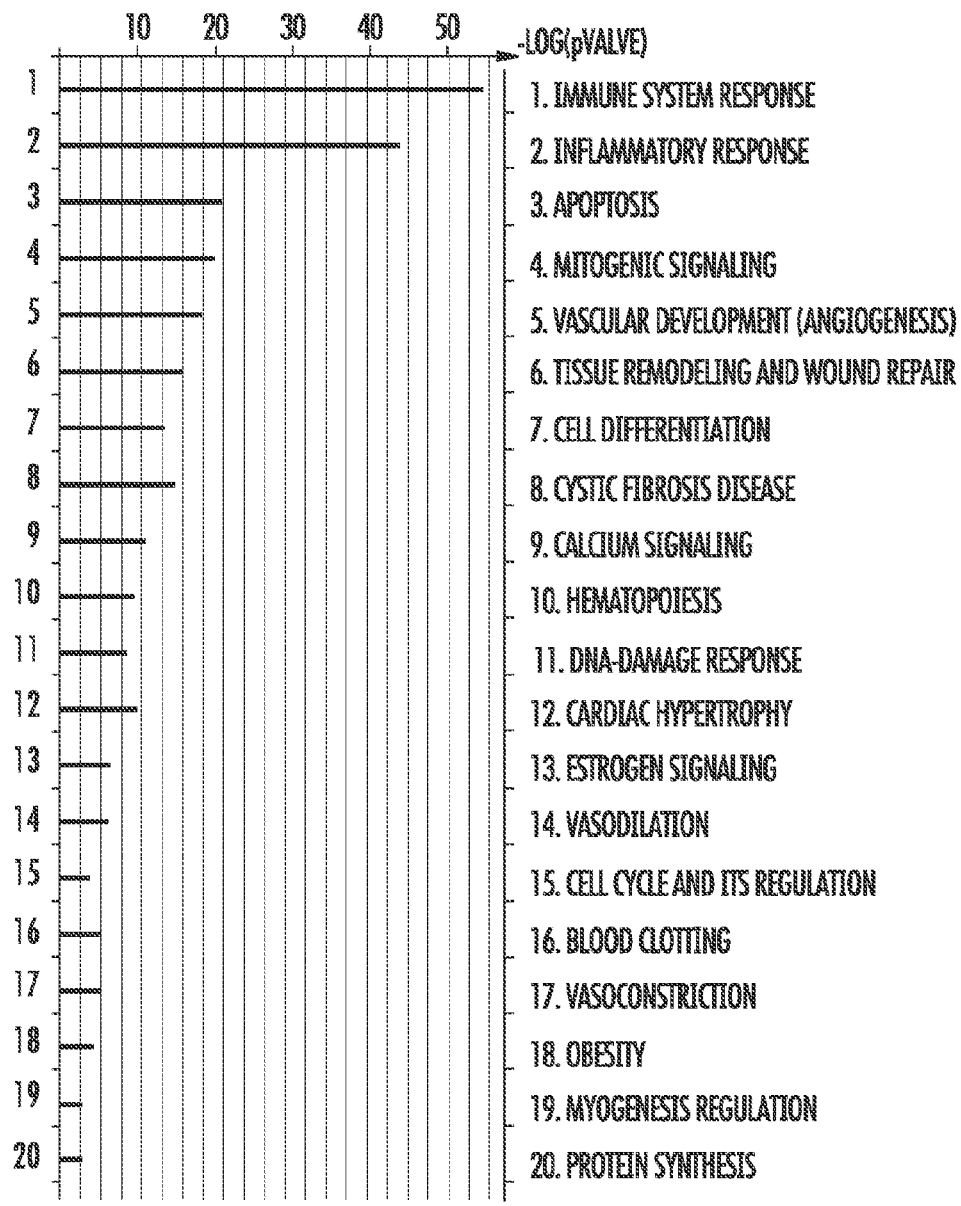
FIG. 2B is an ontology distribution of genes affected in HDAC6KD cells. Ontology report generated by "The database for Annotation, Visualization and Integrated Discovery (DAVID)". Quantitative real time PCR validation.
Figure 2C:
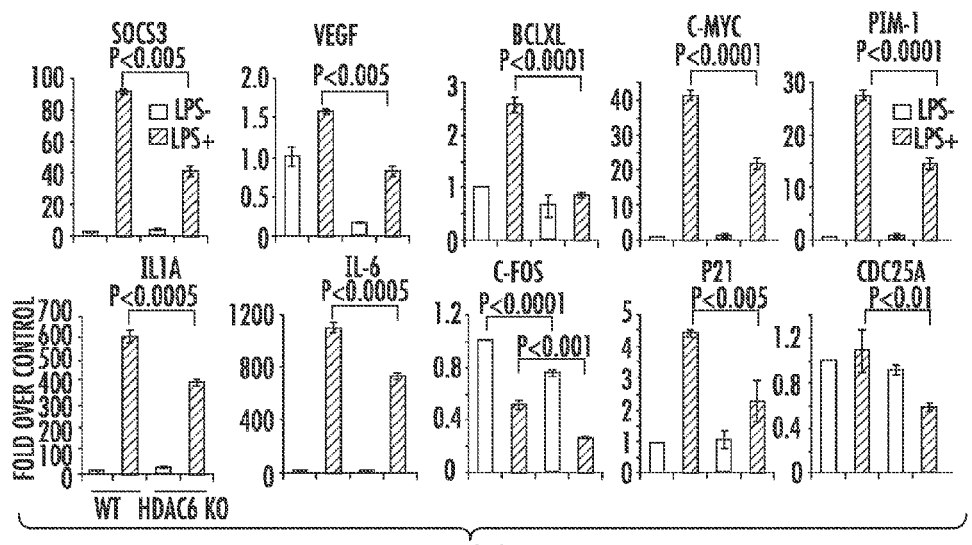
FIG. 2C contains bar graphs showing gene expression in RAW264.7 NT and HDAC6KD cells ($2 \times 10^6$/well) untreated or stimulated with LPS (1 μg/ml) for 2 hrs, then total RNA was isolated to analyze the expression of genes affected by HDAC6KD. GAPDH was used as control. The results are expressed as a percent over control cells and calculated by the Pfaffl equation. Three experiments were performed with similar results. Error bars represent standard deviation from triplicates.

HDAC6 is a 131 KDa protein considered to be a key regulator of cytoskeleton dynamics and cell-cell interactions (Hubbert, C., et al. Nature 417:455-458 (2002); Valenzuela-Fernández, A., et al. Trends in Cell Biology 18:291-297 (2008)). Although this HDAC is predominantly cytoplasmic, studies have demonstrated its presence in nuclear extracts and its recruitment to gene promoter regions (Toropainen, S., et al. J Mol Biol. 400:284-294 (2010)). HDAC6 has been reported to be over-expressed in several cancer types, including ovarian cancer, prostate cancer and acute myeloid leukemia (AML) (Aldana-Masangkay, G. I., et al. J Biomed Biotechnol 2011:875824 (2010)). As shown in FIG. 1, HDAC6 is also over-expressed in several melanoma tumors. Recently, HDAC6 has been implicated in other cellular processes, including the modulation of immune responses (Serrador, J. M., et al. Immunity 20:417-428 (2004); Kalin, J. H., et al. J Med Chem. (2012)). This is consistent with icroarray data analyzing the gene expression profile (GEP) of untreated and LPS-treated RAW264.7 macrophages in which HDAC6 was knocked down using specific shRNA (HDAC6KD) or treated with control shRNA non-coding for any mouse mRNA (non-target, NT). 1542 genes were down-regulated and 775 were up-regulated in HDAC6KD cells (FIG. 2A). Their ontology distribution revealed important changes in both immune-related and apoptosis/cell cycle control genes (FIG. 2B). An interesting finding gathered from the GEP analysis was the down-regulation of almost every STAT3 target gene in HDAC6KD cells, suggesting the potential participation of STAT3 in the outcome that is observed in the absence of HDAC6 (FIG. 2C). Similarly, several previously described c-Jun target genes were down-regulated, suggesting that the inhibition of HDAC6 affected the MAPK pathway as well.

STAT3 activation can be achieved by different stimuli and is often the point of convergence for many signaling pathways triggered by cytokines, growth factors and other stimuli, being considered by itself an oncogene. Hyperactivation and/or constitutive activation of STAT3 has been found in a wide range of tumors and transformed cell lines. In particular, constitutively active STAT3 has been reported in more than 70% of solid and hematological tumors, including melanoma and lung cancer (Kortylewski, M., et al. Cancer Metastasis Rev 24:315-327 (2005); Yu, H., et al. Nat Rev Immunol. 7:41-51 (2007)). There are numerous reports describing the effect of STAT3 manipulation upon tumor growth, survival, invasiveness, metastatic potential, angiogenesis, and immune-escape. In fact, the over-expression of constitutive active STAT3 (STAT3c) leads to the immortalization of non-malignant cell lines (Regis, G., et al. Seminars in Cell & amp; Developmental Biology 19:351-359 (2008)). Hyperactivity of STAT3 also deregulates the expression of several important cytokines such as IL-6 and IL-10. Interestingly, HDAC6 interacts with STAT3 and is recruited to and regulates the expression of IL10 and IL6 genes.

Figure 3A:
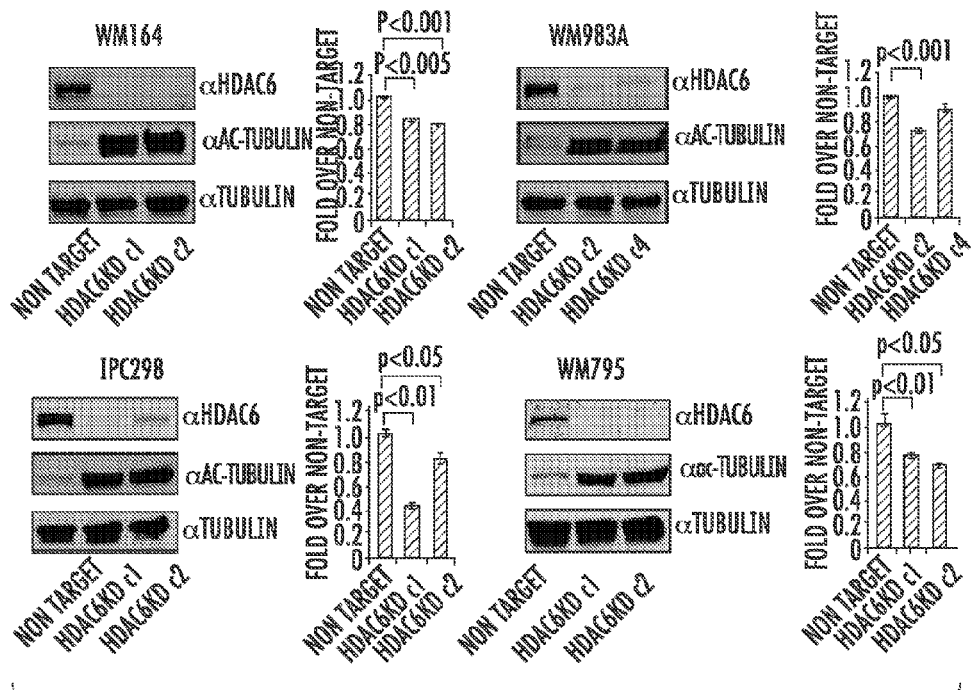
FIGS. 3A to 3B show HDAC6 knock-down decreases STAT3 activation.
Figure 3B:
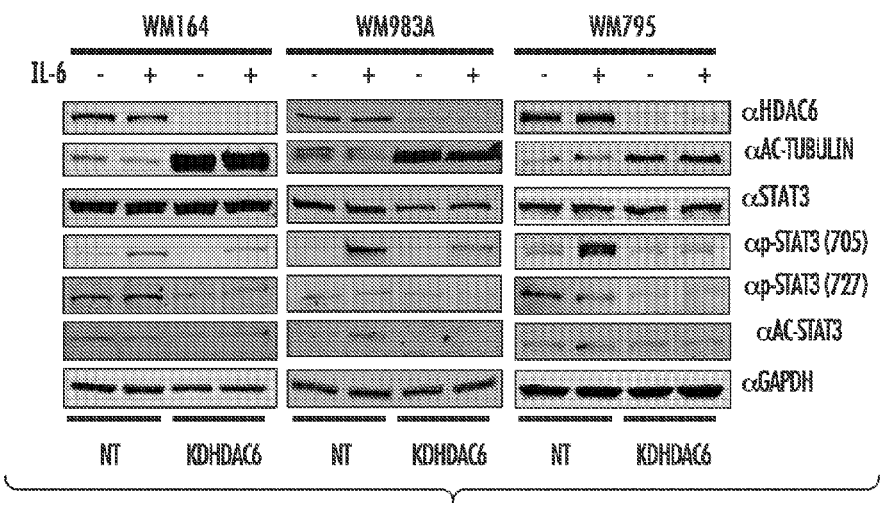

Given these findings, as well as the well known role of STAT3 deregulation in the pathogenesis of melanoma, a study was conducted to determine whether the absence of HDAC6 affected the activation of the JAK/STAT3 pathway in melanoma cells. By using lentiviral HDAC6 shRNA, stable HDAC6KD cell lines were generated in several melanoma cell lines carrying either NRAS (SKMEL21, SKMEL103, IPC298) or BRAF (WM164, WM35, WM983, WM795) mutations. Of note, all HDAC6KD cell lines demonstrated slower proliferation rates when compared with their respective non-target shRNA control stable cell lines (FIG. 3A, representative from all cell lines analyzed). When the activation of the Jak2/STAT3 pathway was analyzed in these HDAC6KD cells, there was diminished phosphorylation of the Ser-727 and Tyr-705 residues of STAT3 upon IL-6 stimulation (similar results obtained upon IL-10 and IFNγ stimulation) (FIG. 3B, lines 4 and 5). Recent reports have assigned the key role of acetylation over the activation of STAT3, a process mediated mainly by CBP/p300 acetylation and class I HDAC deacetylation (Togi, S., et al. Biochem Biophys Res Commun. 379:616-620 (2009); Lee, H., et al. Proc Natl Acad Sci USA 109:7765-7769 (2012). Taking this antecedent into consideration, the acetylation status of STAT3 was analyzed. However, major differences in its acetylation status in the absence of HDAC6 (FIG. 1B, line 6) was did not detected, suggesting that the effect of HDAC6 on its activation does not depend on a direct deacetylation of STAT3.

Figure 4A:
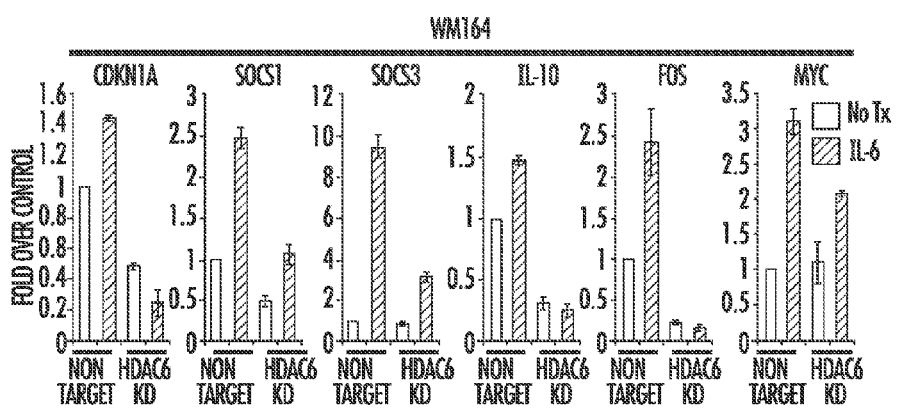
FIG. 4A shows expression of STAT3 target genes in HDAC6KD and NT WM164 cells stimulated with IL-6 by qRT-PCR.

STAT3 must be phosphorylated in order to be translocated to the nucleus and properly exert its function over target genes (Ihle, J. N. Current opinion in cell biology 13:211-217 (2001)). Therefore, the diminished phosphorylation of STAT3 observed in the absence of HDAC6 might interfere with the activation of STAT3 target genes. To answer this question well defined STAT3 target genes were selected and their expression measured upon IL-6 stimulation. An important reduction in the mRNA was observed for all tested genes, including CDKN1A, SOCS1, SOCS3, IL10, FOS and MYC (FIG. 4A).

Figure 4B:
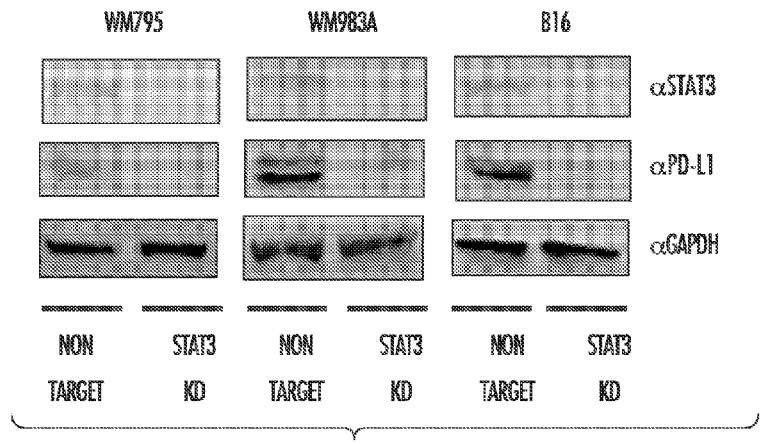
FIG. 4B shows the expression of STAT3, PDL1, and GAPDH in STAT3KD and NT melanoma cells by western blot.
Figure 5A:
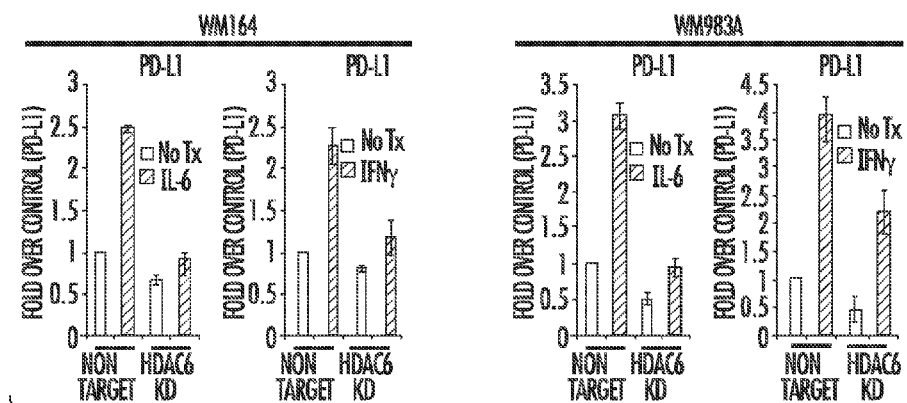
FIGS. 5A and 5C show the expression of PDL1 evaluated in HDAC6KD and NT melanoma cells by qRT-PCR (FIG. 5A) or Flow cytometry (FIG. 5C).
Figure 5B:
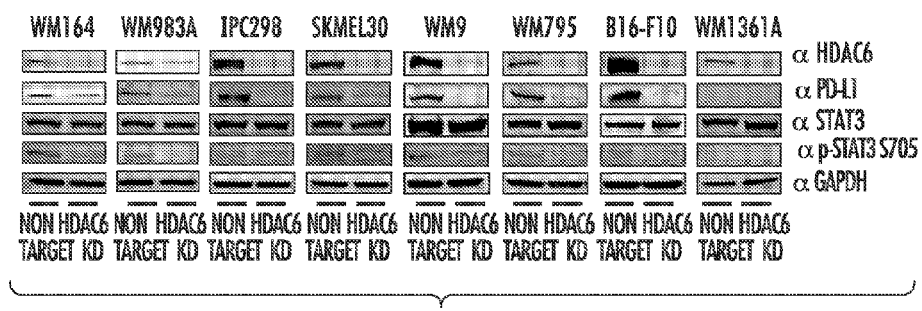
FIG. 5B shows the expression of HDAC6, PDL1, STAT3, pSTAT3, and GAPDH in HDAC6KD and NT melanoma cells by western blot.
Figure 5C:
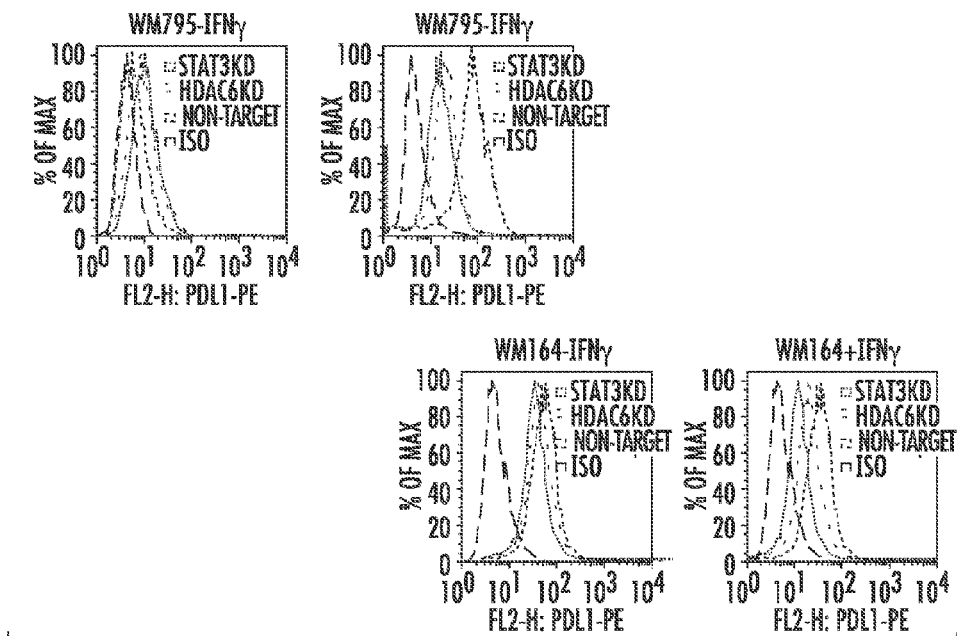

The GEP microarray data in HDAC6KD macrophages revealed changes in immune related genes. Among these genes, an 8-fold decrease in the expression of PDL1 (CD274) was observed. This finding was validated by qRT-PCR in primary macrophages isolated from wild type and HDAC6KO mice stimulated with IL-6. PDL1 and PD-L2 are ligands for PD-1, a co-stimulatory molecule that plays an inhibitory role in regulating T-cell activation. Specifically, the interaction between PDL1 (from cancer cells) and the PD-1 present on T-cells inhibits T-cell activation, proliferation, and promotes T-cell apoptosis. The importance of the interaction of PDL1 and PD-1 has been extensively described in in vitro and in vivo models, as well as in clinical studies (Topalian, S. L., et al. Curr Opin Immunol 24:207-212 (2012)), with promising antitumor results in several preclinical and clinical studies involving PDL1 blocking antibodies (Pardoll, D. M. Nat Rev Cancer 12:252-264 (2012)). Furthermore, PDL1 expression is correlated with poor clinical prognosis for a number of cancers including renal, breast, and esophageal cancers. As a result, increased PDL1 expression by cancer cells remains a fundamental escape mechanism from host immunity, and the understanding of molecular mechanisms modulating PDL1 expression could lead to improved treatments for cancer patients. The expression of PDL1 is controlled by several pathways, including those activated by IL-6, IL-10, GM-CSF, TLRs, interferons and TNFα (Francisco, L. M., et al. Immunol Rev 236:219-242 (2010)). In addition, recent reports have described STAT3 as one of the main regulators of PDL1 expression (Wolfle, S. J., et al. Eur J Immunol 41:413-424 (2011)). This finding was also verified in by evaluating the expression of PDL1 in human and mouse melanoma cells lacking STAT3 (STAT3KD) (FIG. 4B). Therefore, HDAC6 could be an indirect regulator of the expression of PDL1 in melanoma via STAT3 modulation. Taking this observation into consideration, the expression of PDL1 in HDAC6KD human melanoma cells stimulated with IL-6 was evaluated by qRT-PCR (FIG. 5A). When compared to non-target controls, decreased expression of PDL1 was observed. This result was also validated by measuring the PDL1 protein by western blot (FIG. 5B) and flow cytometry (FIG. 5C).

HDAC6 is recruited to regulatory sequences in gene promoters such as MYC (Toropainen, S., et al. J Mol Biol. 400:284-294 (2010)), glucocorticoid receptor (Govindan, M. V. J Biol Chem. 285:4489-4510 (2010)) and estrogen receptor α-inducible genes (Palijan, A., et al. J Biol Chem. 284:30264-30274 (2009)). However, there is no evidence showing that HDAC6 is directly affecting the acetylation status of chromatin. In fact, the deacetylation of histones by HDAC6 has only been demonstrated by in vitro assays (Todd, P. K., et al. PLoS Genet 6:e1001240 (2010)). Thus, the transcriptional regulatory effects observed for HDAC6 could be mediated by other regulatory factors recruited along with this deacetylase to specific DNA sequences. This hypothesis suggests that HDAC6 may be a regulator of the activation status of these transcription factors, perhaps by modulating their acetylation and/or phosphorylation. HDAC6 and STAT3 are recruited to the same region of the IL-10 promoter, and the recruitment of HDAC6 is impaired when cells are treated with the STAT3 inhibitor CPA-7. Moreover, the recruitment of STAT3 to the IL-10 promoter diminishes considerably in HDAC6KD cells, suggesting that the down-regulation of PDL1 expression might be a consequence of the effect of HDAC6 on STAT3 activation.

Figure 6A:
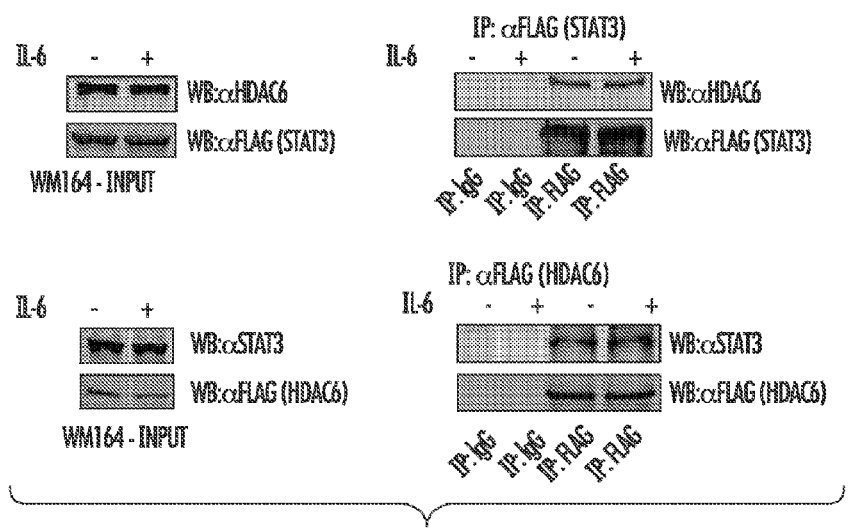
FIG. 6A shows either Flag-STAT3 (top) or Flag-HDAC6 expressed in WM164 cells and subjected to immunoprecipitation. HDAC6 and STAT3 were evaluated in the immunoprecipitated fraction.
Figure 6B:
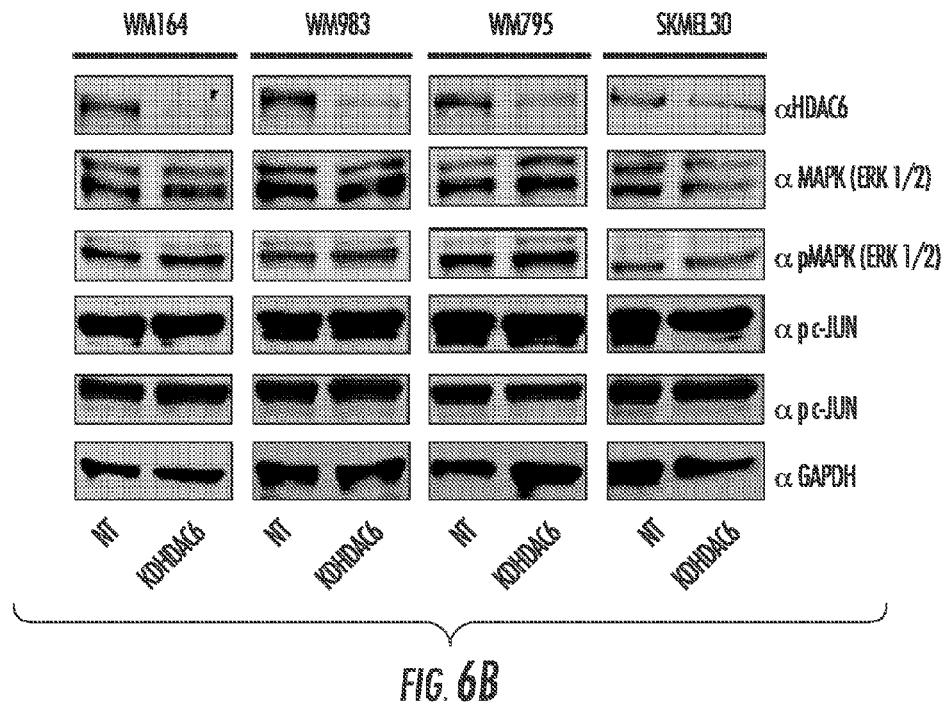
FIG. 6B shows the expression of HDAC6, MAPK, pMAPK, c-JUN, p c-JUN, and GAPDH evaluated in HDAC6KD and NT melanoma cells by western blot.
Figure 6C:
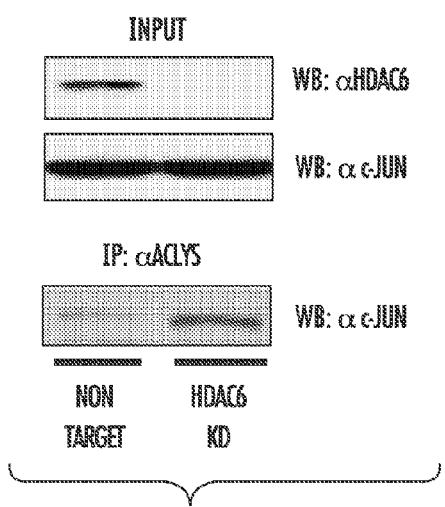
FIG. 6C shows non-target and HDAC6KD cells subjected to immunoprecipitation using an anti-total acetyl-lysine antibody and evaluated for the presence of c-JUN in the immunoprecipitated fraction.

Another potential regulator of the transcriptional regulation of PDL1 is c-Jun. The inhibition of the MEK cascade and the subsequent c-Jun inactivation may lead to the down-regulation of PDL1. This phenomena is also observed in BRAF inhibitor-resistant melanoma cells (Jiang, X., et al. Clin Cancer Res 19:598-609 (2013)). HDAC6 interacts with STAT3 and c-Jun to form stable protein complexes, as detected by co-immunoprecipitation (FIG. 6A). Additionally, HDAC6 does not interfere with the phosphorylation of Erk or c-Jun in melanoma cells (FIG. 6B), suggesting that its effect over the activation of c-Jun target genes could involve another molecular mechanism. In this regard, it has been proposed that the acetylation of c-Jun modulates its transcriptional activity over target genes. Specifically, the acetylation of Lys271 of c-Jun facilitates its interaction with co-repressors and the subsequent repression of its target genes (Vries, R. G., et al. EMBO J 20:6095-6103 (2001)). To further explore this possibility, the acetylation status of c-Jun in the absence of HDAC6 was evaluated, demonstrating an important increase in its acetylation, suggesting the participation of HDAC6 in this process (FIG. 6C).

Besides STAT3 and c-Jun, there are no known transcriptional regulators or chromatin modifiers affecting the PDL1 promoter. Therefore, it is highly desirable to perform a more comprehensive analysis of the transcriptional regulation of this gene. Further understanding of the PDL1 promoter could identify targets to control its expression, which in turn could be used as a therapeutic option to ameliorate cancer immune evasion mediated by PDL1.

Figure 7A:
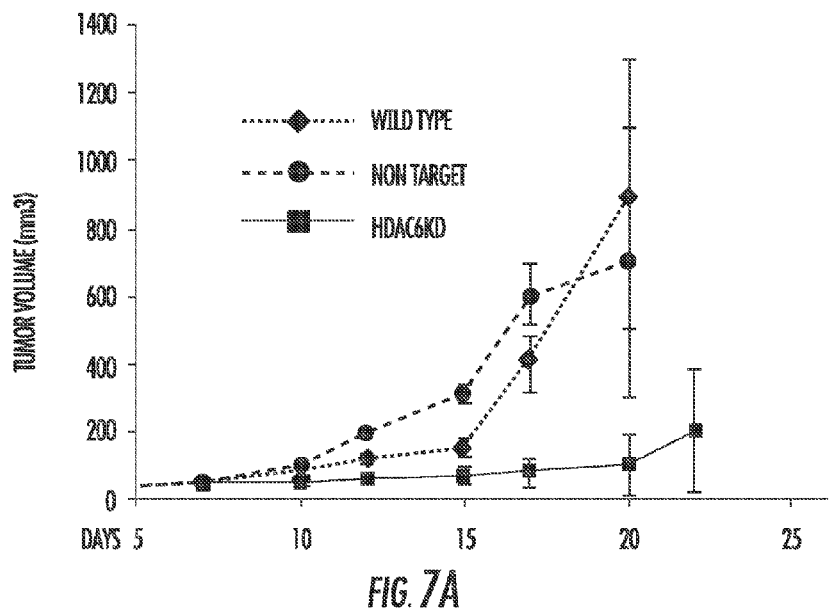
FIG. 7A shows the in vivo growth of HDAC6KD melanoma cells (and control non-target and WT melanoma cells) in immune competent C57BL/6 mice.
Figure 7B:
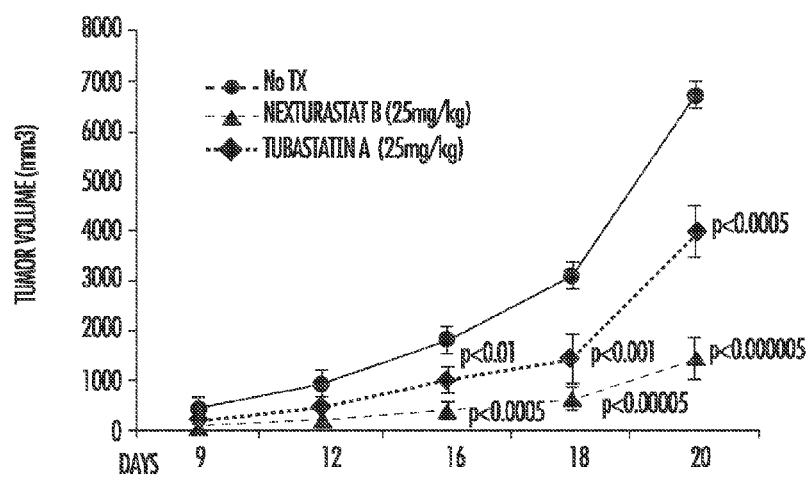
FIG. 7B shows in vivo growth of B16 cells in C57BL/6 mice treated with Nexturastat.
Figure 7C:
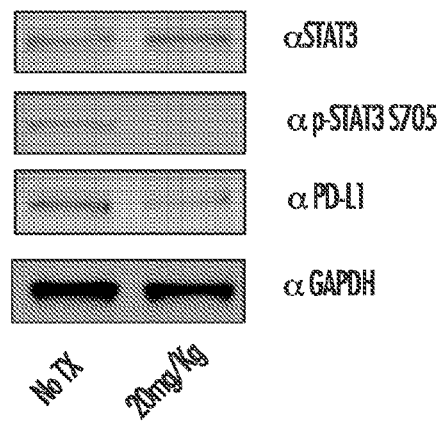
FIG. 7C shows protein levels of STAT3, pSTAT3, PDL1, and GAPDH in tumor samples treated with Nexturastat.
Figure 7D:
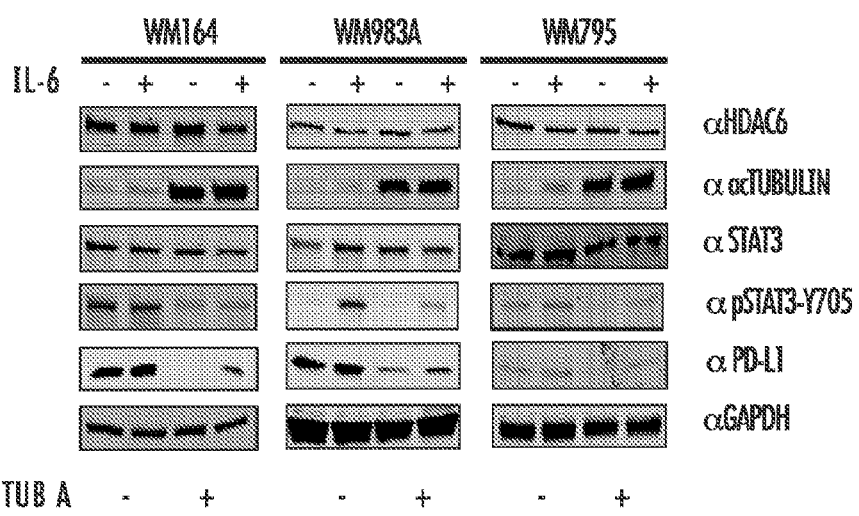
FIG. 7D shows protein expression in melanoma cells treated with the HDAC6inh Tubastatin A for 48 hours.
Figure 8A:
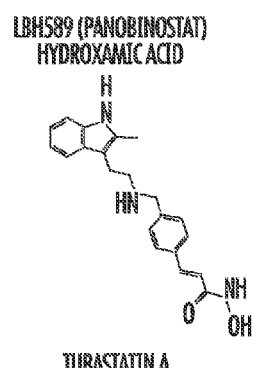
FIG. 8A shows the structure of HDAC inhibitors tested.
Figure 8A:
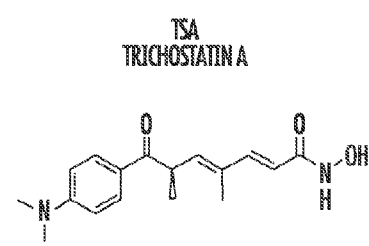
Figure 8A:
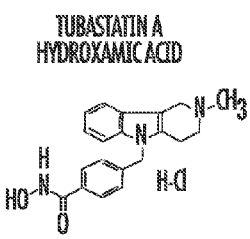
Figure 8A:
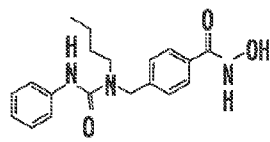
Figure 8B:
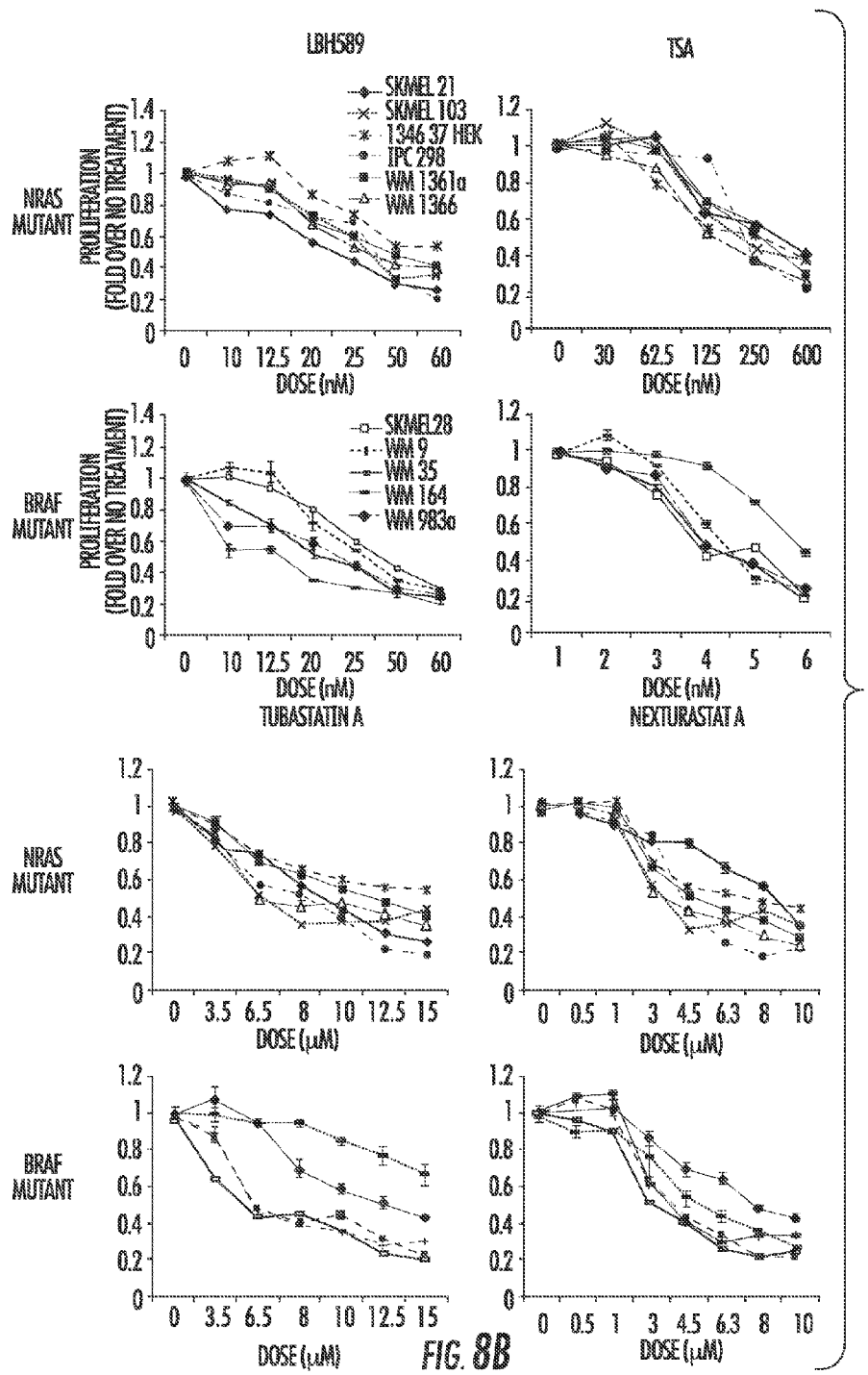
FIG. 8B shows cell viability of melanoma cells incubated with LBH589, TSA, Tubastatin A, or Nexturastat A at different concentrations for 24 hrs. Error bars represent standard deviation from triplicates. This figure is representative of two independent experiments.
Figure 8C:
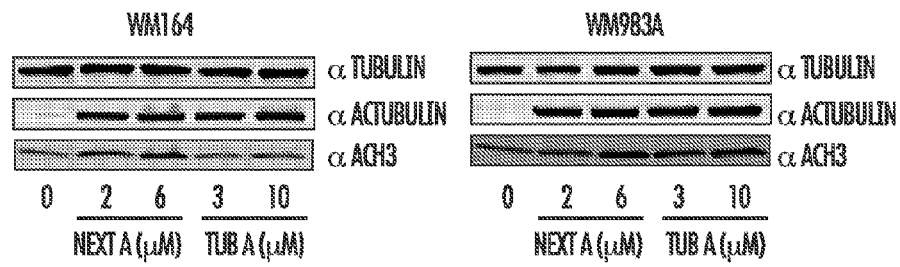
FIG. 8C shows tubulin, acetyl-tubulin and acetyl-histone3 expression in BRAF-mutated melanoma cell lines treated with HDAC6 inhibitors.
Figure 9A:
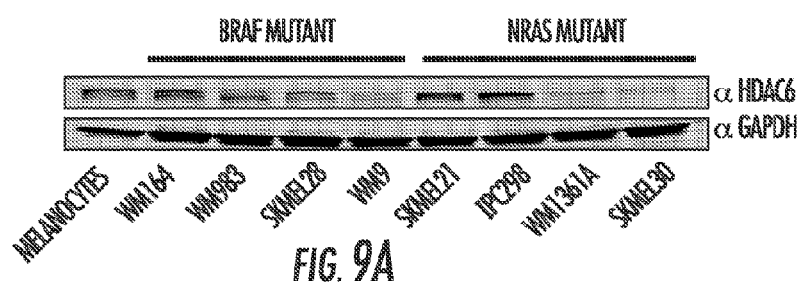
FIGS. 9A and 9B show HDAC6 profile of melanoma cell lines.
Figure 9B:
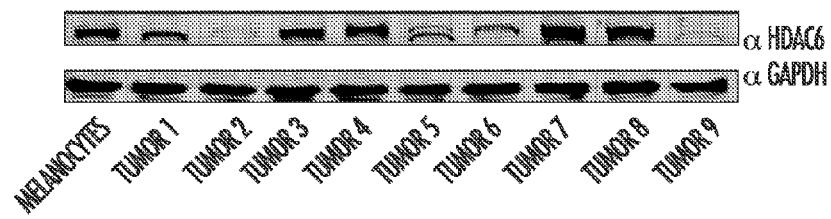

Highly selective HDAC6 inhibitors (HDAC6inh) are currently available, which make this deacetylase a very attractive target to pursue as a therapeutic option. In this context, selective HDAC6 inhibitors, alone or in combination with other agents, are currently under evaluation in clinical trials, including the ongoing Phase 2 Multiple Myeloma clinical trial using the HDAC6inh ACY1215, which has shown important anti-tumor activity in preliminary studies (Santo, L., et al. Blood 119:2579-2589 (2012)). Pan-HDAC inhibitors (pan-HDACi) slows the proliferation and improves the immunogenicity of melanoma cells (Woods, D. M., et al. Melanoma Res (2013)). However, the non-selective nature of pan-HDACi makes the assumption of the specific participation of HDACs on these processes impossible. As shown in FIG. 2A, HDAC6KD melanoma cells have a slower rate of proliferation when compared to their respective controls. This result was mirrored in melanoma cell lines treated with selective HDAC6 inhibitors. The next step was identifying if HDAC6KD would affect the growth of melanoma cells in vivo. Thus, a delayed tumor growth of HDAC6KD B16 murine melanoma cells was observed when compared to wild type or non-target controls (FIG. 7A). A similar result was obtained in another experiment injecting wild type B16 melanoma cells into C57BL/6 mice treated daily with 20 mg/kg of the HDAC6inh Nexturastat A or Nexturastat B (FIG. 7B). The amount of PDL1 and activation of STAT3 was decreased in tumors isolated after the in vivo treatment with HDAC6inh (FIG. 7C). This observation was also made in melanoma cell lines treated with HDAC6inh (FIG. 7D), suggesting the potential role of HDAC6 in this process, and evidence that its deacetylase activity is necessary to mediate this effect.

This delay in tumor growth in HDAC6KD melanoma cells and melanoma cells treated with HDAC6inh could be a reflection of their diminished proliferation (as evidenced in in vitro studies) and/or an increase in their immunogenicity leading to improved immune recognition and clearance.

Conclusions

The expression of PDL1 has been shown to be induced in almost every type of cancer, including solid tumors such as melanoma, and it has been proposed that this could be one of the main mechanisms used by cancer cells to acquire resistance to T-cell killing, by activating the negative regulatory pathway PD-1 in T-cells. This is particularly important in the resistance to BRAF inhibitors, phenomena frequently associated with an up-regulation of the expression of PDL1 (Jiang, X., et al. Clin Cancer Res 19:598-609 (2013)). Therefore, the inhibition of PDL1 expression could offer new therapeutic options to prevent or revert the resistance to current therapies aiming to improve the immune recognition of cancer cells (i.e. PDL1, PD-1, and CTLA-4 blocking antibodies).

Example 2: Histone Deacetylase 6 (HDAC6) as a New Target Modulating the Proliferation and Immune-Related Pathways in Melanoma Histone deacetylases (HDACs), originally described as histone modifiers, have more recently been demonstrated to modify a variety of other proteins involved in diverse cellular processes unrelated to the chromatin environment. This includes the deacetylation of multiple non-histone targets, such as proteins involved in cell cycle/apoptosis and immune regulation. Specifically, HDACs have garnered significant interest due to the availability of drugs that selectively inhibits HDACs. The pharmacological or genetic abrogation of a single HDAC, HDAC6, modifies the immunogenicity and proliferation of melanoma in both in vitro and in vivo models.

Figure 10A:
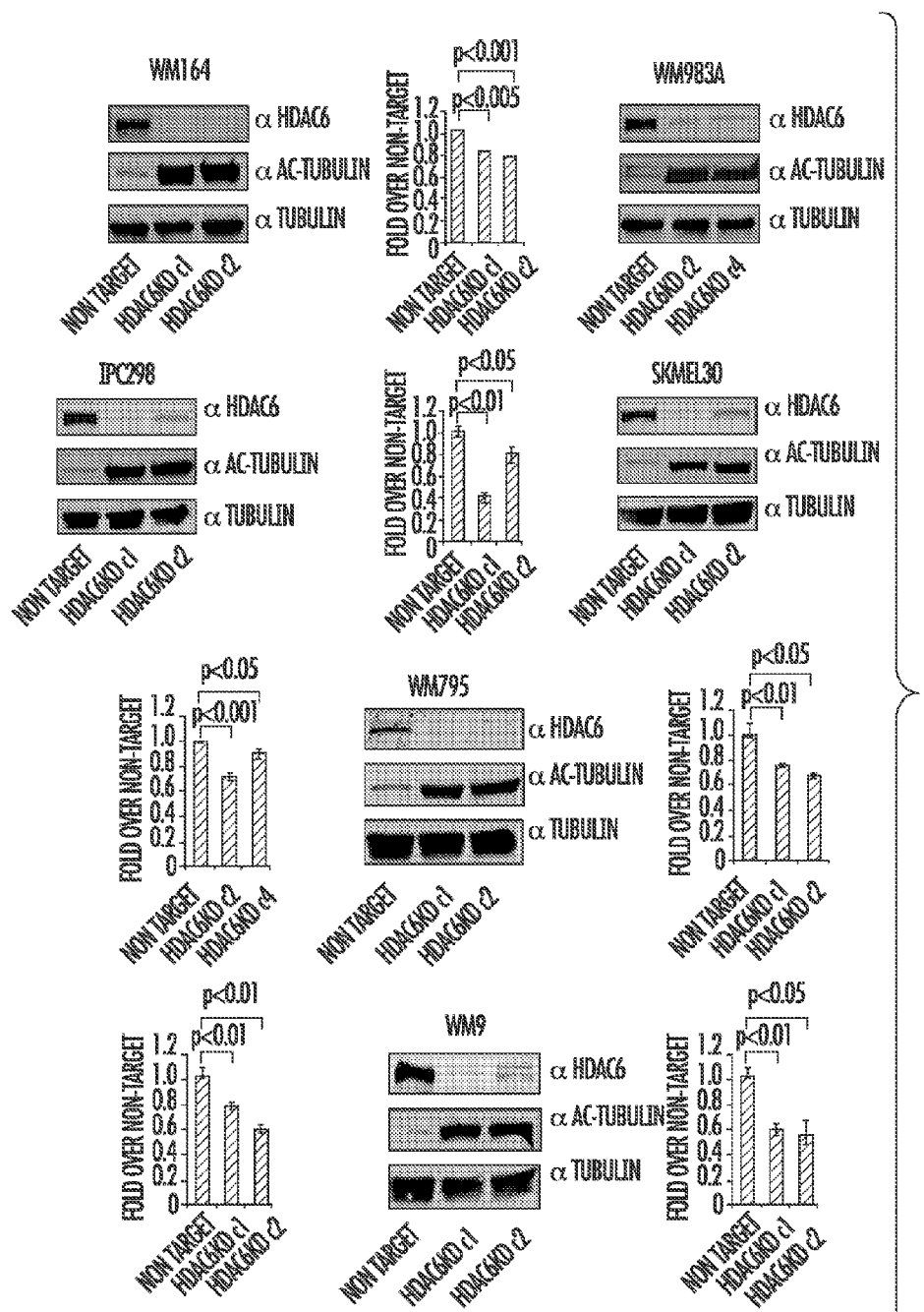
Figure 12A:
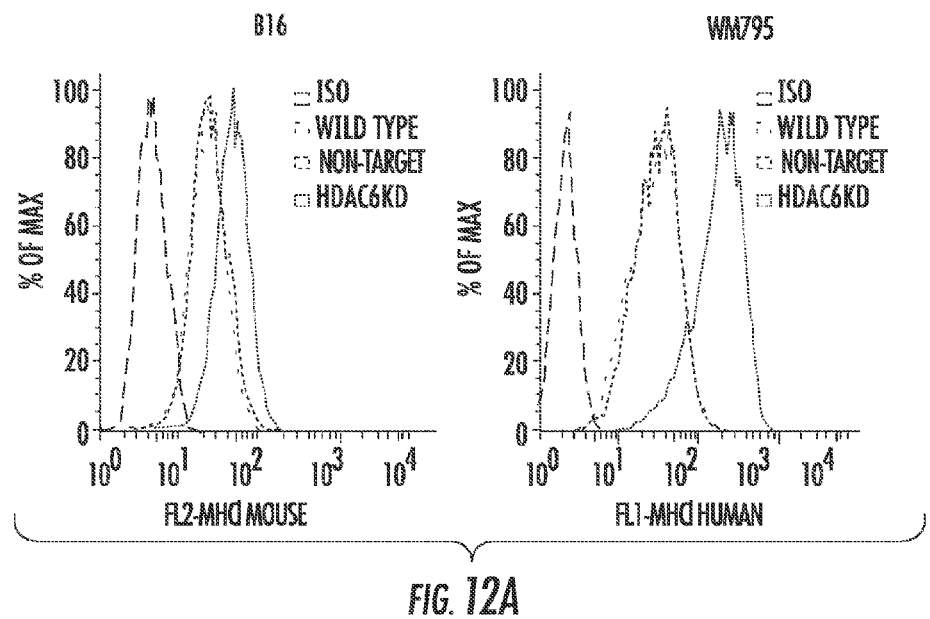
Figure 12B:
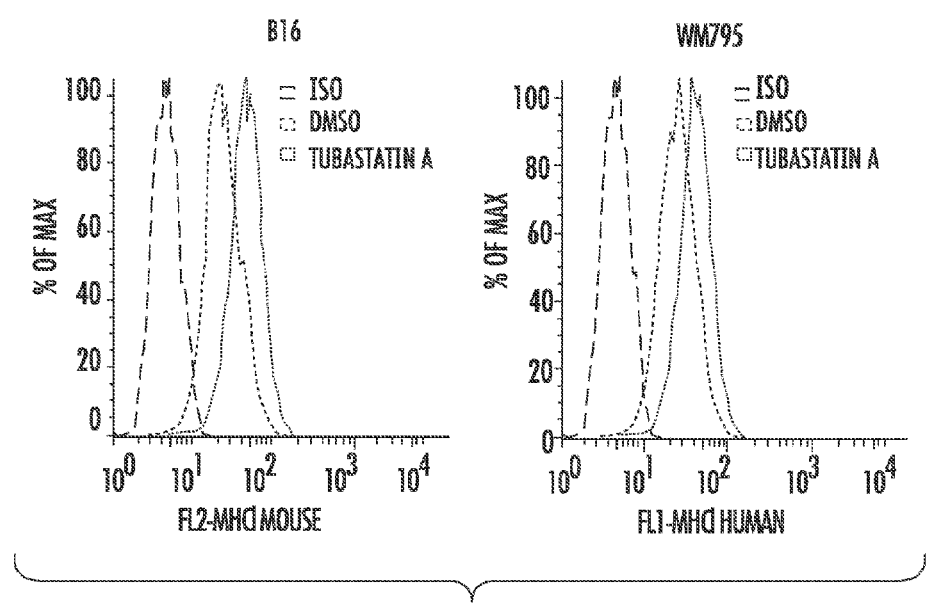
FIG. 12B shows MHC I expression in wild type melanoma cell lines treated in vitro with Tubastatin A (3 μM) for 48 hours.

Using specific HDAC6 inhibitors (HDAC6i), decreased proliferation and G1 cell cycle arrest was observed in all melanoma cell lines measured by MTS assay and flow cytometry (FIG. 8). These results were also observed in stable HDAC6 knockdown melanoma cell lines (HDAC6KD) generated by specific lentiviral shRNA for HDAC6 (FIG. 10D). In addition to the effects observed in proliferation and apoptosis after inhibiting HDAC6, also shown are important changes in the expression of immune-related pathways, including increased expression of MHC (FIG. 12), co-stimulatory molecules, and specific melanoma tumor associated antigens such as gp100, MART-1, Tyrp1 and Tyrp2 (FIG. 11A-11C).

Figure 13A:
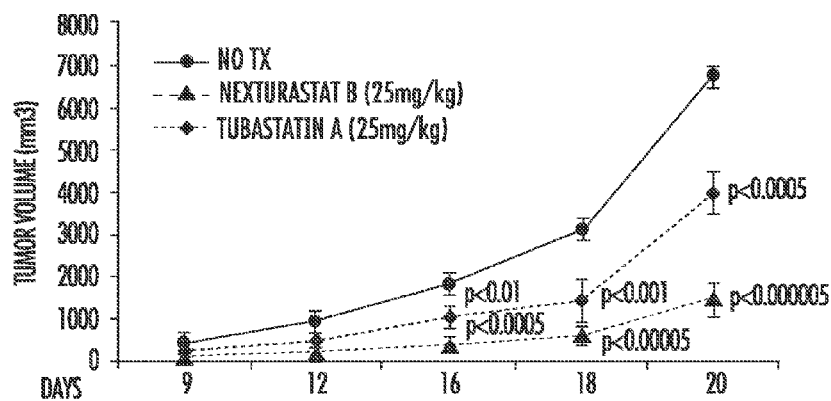
FIG. 13A shows in vivo tumor growth of C57BL/6 mice injected subcutaneously with B16 WT cells. Mice were either untreated or treated with the HDAC6 inhibitor Nexturastat B or Tubastatin A via daily intraperitoneal injection.
Figure 13B:
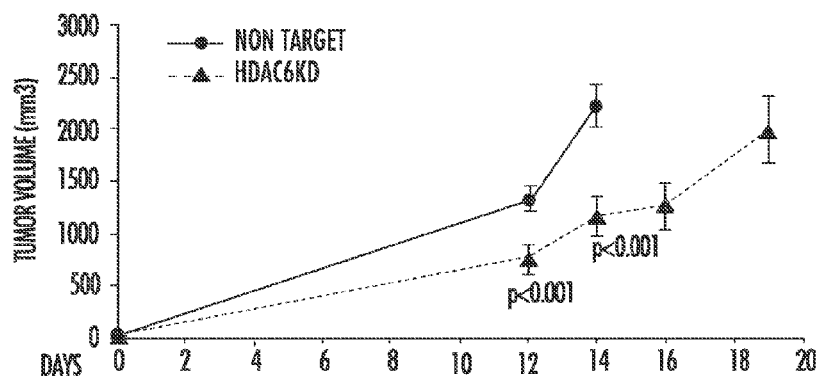
FIG. 13B shows in vivo growth of C57BL6/mice injected with B16 HDAC6KD or NT melanoma cells.
Figure 13C:
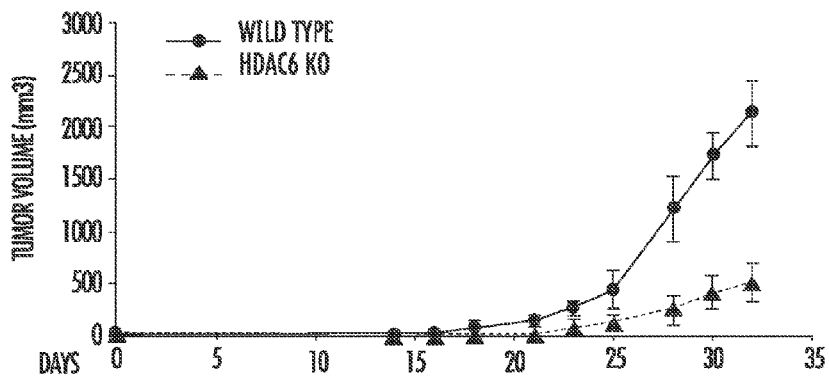
FIG. 13C shows B16 growth in HDAC6 KO C57BL/6 mice and WT control.
Figure 14A:
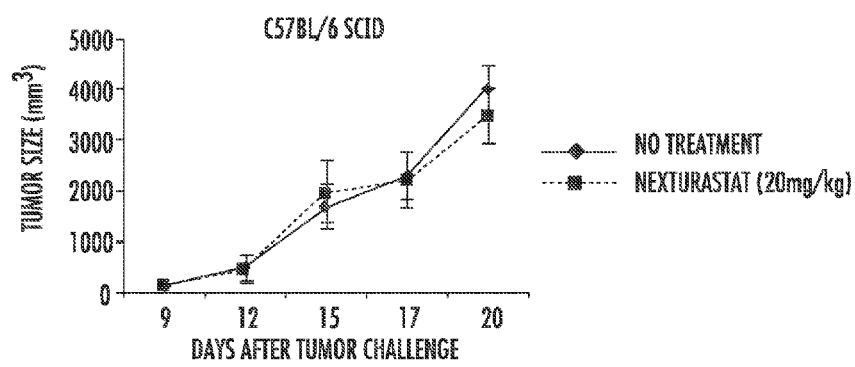
FIGS. 14A and 14B show differences in growth of melanoma cells after HDAC6 inhibition in altered immune systems.
Figure 14B:
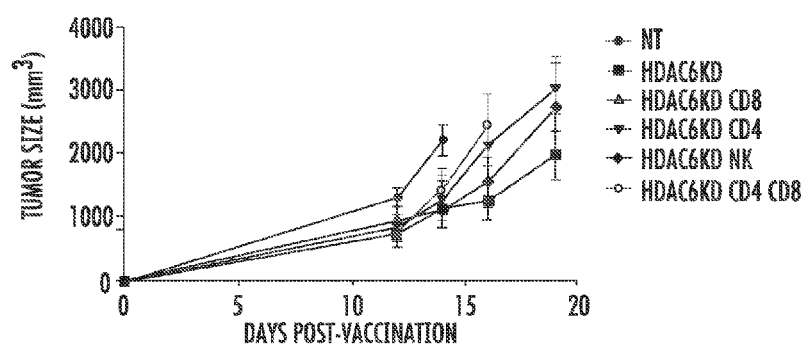

These in vitro results were further supported by in vivo tumor growth studies. Delayed tumor growth of inoculated B16 melanoma cells was observed in C57BL/6 mice treated with selective HDAC6i (FIG. 13). A similar outcome was identified after inoculation of HDAC6KD B16 melanoma cells in C57BL/6 mice (FIG. 14A). Such an effect was reverted partially in CD4+ and CD8+ depleted C57BL/6 mice challenged with HDAC6KD cells (FIG. 14B), suggesting that the disruption of HDAC6 enhances immune system recognition of melanoma cells. This delay in tumor growth could be a reflection of their diminished proliferation and an increase in their immunogenicity leading to improved immune recognition and clearance. These studies provide critical insights into the molecular pathways that are involved in the regulatory role of HDAC6 in cell proliferation, survival, and cytokine signaling of human melanoma cells. Collectively, these data have identified HDAC6 as an attractive therapeutic target in melanoma.

Example 3: Histone Deacetylase 6 (HDAC6) as a Regulator of PDL-1 Expression Through STAT3 Modulation in Melanoma In spite of the progress made in the understanding of the cell biology, genetics and immunology of melanoma, the outcome for patients with advanced-stage disease has remained poor with a median survival ranging from 2-16 months. Some optimism was recently provided in metastatic melanoma by the improved clinical outcomes observed in patients receiving PDL-1 blocking antibodies.

A better understanding of the environmental, genetic and epigenetic factors limiting the efficacy of melanoma immunotherapy will provide appropriate partner(s) for combination with Ipilimumab or PD1/PDL1 antibodies. Among the epigenetic factors, one member of the histone deacetylase family, HDAC6, is shown to play a critical role not only in the regulation of survival/apoptosis of melanoma cells but also in limiting their immunogenicity and recognition by immune effector cells. In particular, disclosed is a major role of HDAC6 as a modulator of the immunosuppresive STAT3/IL-6 pathway, resulting in the down-regulation of tolerogenic PDL1 molecules in melanoma cells. By analyzing HDAC6 knock-down melanoma cell lines (HDAC6KD), shown herein is the inactivation of the STAT3 pathway and the subsequent down-regulation of its target genes, including the expression of PDL1. It was also observed that the PDL1 expression and phosphorylation of STAT3 was decreased in melanoma isolated from xenograph tumor growth models after in vivo treatment with specific HDAC6 inhibitors.

Figure 15A:
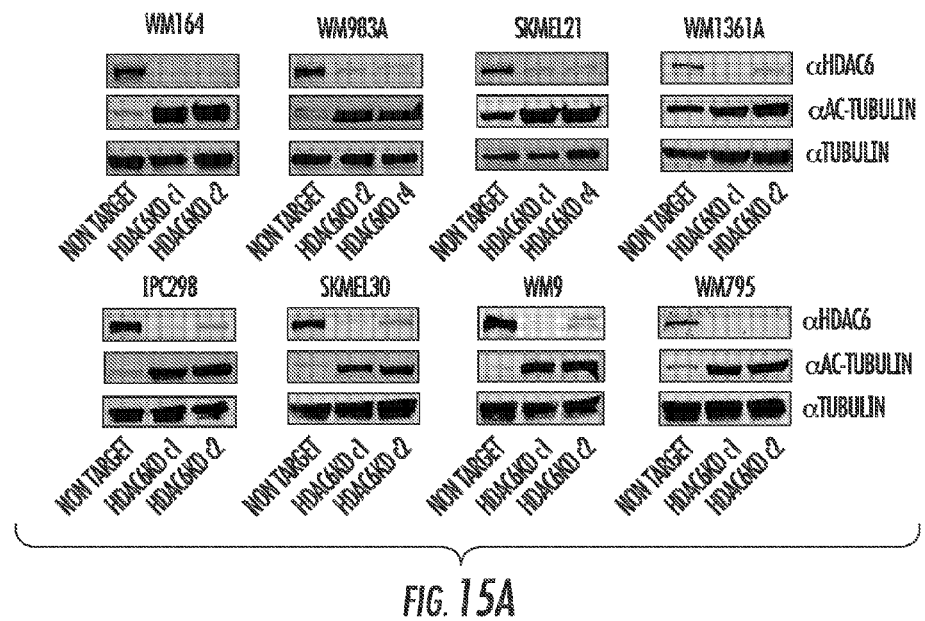
FIGS. 15A and 15B show characterization of HDAC6KD melanoma cells.
Figure 15B:
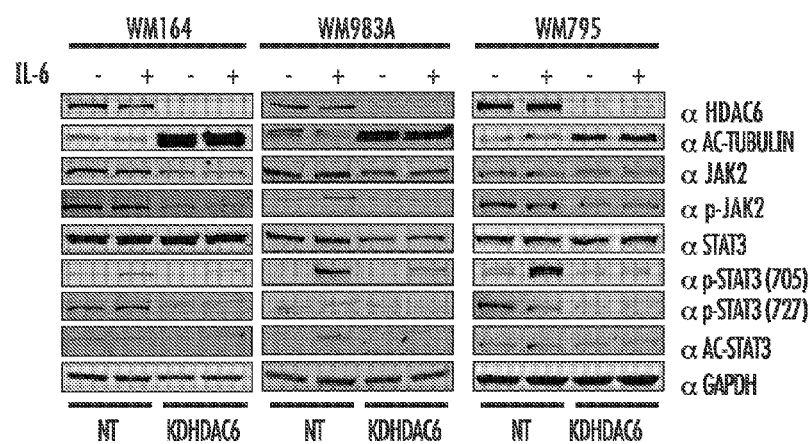

FIG. 15 shows the characterization of HDAC6KD melanoma cells. FIG. 15A shows the generation of melanoma monoclonal cell lines with or without HDAC6 expression. Melanoma cells were transduced with either shRNA coding for HDAC6 or a non-target sequence. Cells were immunoblotted using specific antibodies to HDAC6, tubulin and acetylated tubulin. FIG. 15B shows posphorylation of JAK2 and STAT3 measured in different human melanoma NT or HDAC6KD cell lines after stimulation with IL-6. Cells were lysed and immunoblotted using the specific antibodies above.

FIG. 16 shows quantitative RT-PCR of STAT3 target genes. Total RNA was isolated from melanoma cell lines NT and HDAC6KD before and after treatment with IL-6, and the expressions of STAT3 target genes were analyzed by quantitative RT-PCR. The results are expressed as a percent over control cells, and data was normalized by GAPDH expression. This experiment was performed three times with similar results. Error bars represent standard deviation from triplicates.

Figure 17C:
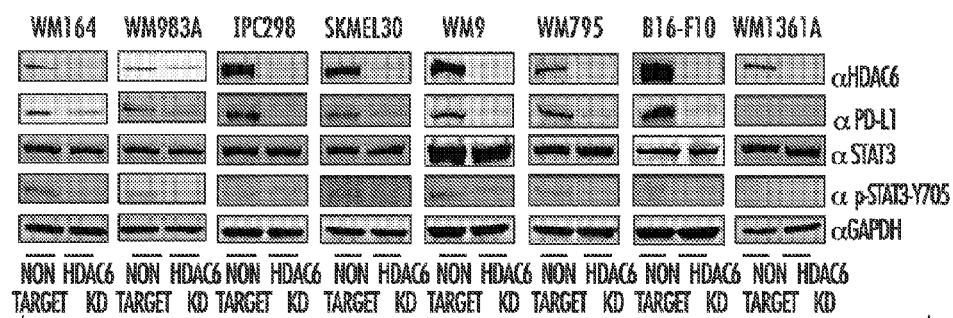

FIG. 17 shows PDL-1 expression in melanoma HDAC6KD: FIG. 17A shows total RNA was isolated from C57BL/mice cells in the HDAC6KO cells versus wild type cells and was measured by qRT-PCR. FIG. 17B shows total RNA isolated from melanoma cell lines NT and HDAC6KD. The expression of PDL1 was analyzed by qRT-PCR after IL-6 (30 ng/ml), IFN-g (100 ng/ml), and DMSO. FIG. 18C shows a Western blot demonstrating decreased PDL1 in HDAC6KD cells.

Figure 18A:
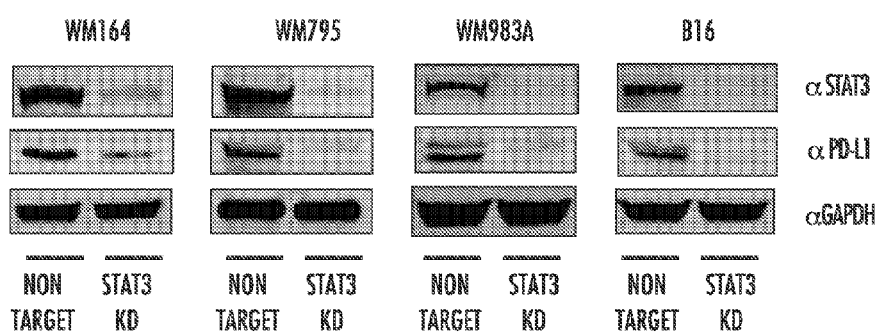
FIGS. 18A and 18B show PDL-1 expression in melanoma STAT3KD and HDAC6KD.
Figure 18:
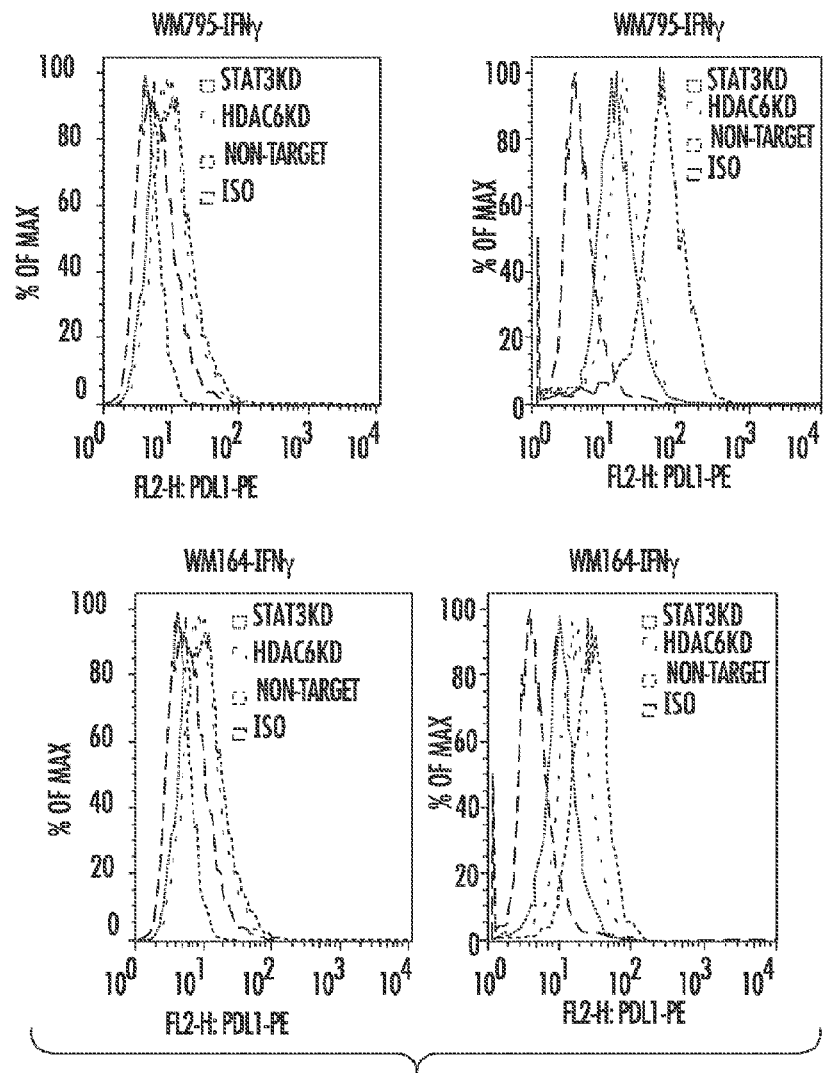

FIG. 18 shows PDL-1 expression in melanoma STAT3KD and HDAC6KD. FIG. 18A shows generation of melanoma monoclonal cell lines with or without STAT3 expression. Cells were immunoblotted using specific antibodies for STAT3, PDL-1 and GAPDH. FIG. 18B shows Flow cytometric analysis for PDL-1 in HDACKD, STAT3KD and non target melanoma demonstrates decreased PDL-1 in HDAC6KD and STAT3KD compared to NT after IFN-g stimulation.

Figure 19:
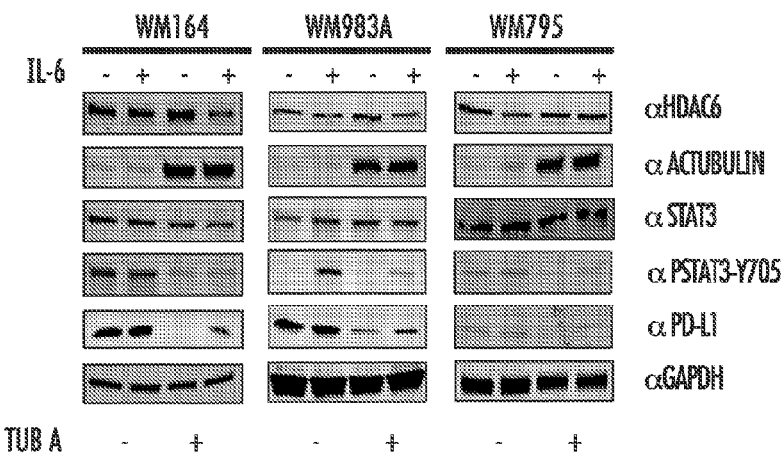
FIG. 19 shows characterization of melanoma cell lines after pharmacologic HDAC6 inhibition. Different melanoma cells lines were incubated with the HDAC6 inhibitor Tubastatin A (12.5 µM) for 24 hours, followed with stimulation by IL-6 (30 ng/ml). Cells were lysed and immunoblotted for HDAC6, acTUBULIN, STAT3, pSTAT3-Y705, PD-L1, and GAPDH.

FIG. 19 shows characterization of melanoma cell lines after pharmacologic HDAC6 inhibition. Different melanoma cells lines were incubated with the HDAC6 inhibitor-Tubastatin A (12.5 µM) for 24 hours, followed with stimulation by IL-6 (30 ng/ml). Cells were lysed and immunoblotted using the specific antibodies listed in the figure.

Figure 20:
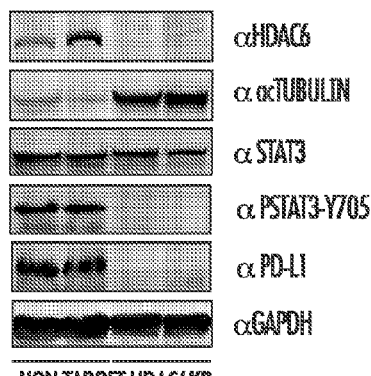
FIG. 20 shows melanoma xenograft analysis. Tumors collected from C57BL mice injected either with B16 NT cells or B16 HDAC6KD were immunoblotted for HDAC6, acTUBULIN, STAT3, pSTAT3-Y705, PD-L1, and GAPDH. Decreased STAT3 phosphorylation and PDL-1 expression are maintained in these tumors.

FIG. 20 shows Melanoma xenograft analysis. Tumors collected from C57BL mice injected either with B16 NT cells or B16 HDAC6KD were lyzed for immunoblotting analysis using the specific antibodies listed in the figure. Decreased STAT3 phosphorylation and PDL-1 expression are maintained in these tumors.

Example 4: Inhibition of Class I Histone Deacetylases Promotes Robust and Durable Enhancement of PDL1 Expression in Melanoma: Rationale for Combination Therapy Histone deacetylase inhibitors (HDACi) have shown remarkable anti-tumor activity, leading to FDA approval of two HDACi for the treatment of CTCL and several others currently at various stages of clinical development for the treatment of both solid and hematological malignancies. Treatment with HDACi results in increased expression of pro-inflammatory promoting surface markers on melanoma cells, promoting enhanced T-cell activation. Recent clinical trial data has shown that blockade of the PD1/PDL1 interaction is effective in the treatment of melanoma, renal cell and non-small cell lung cancer. Importantly, responses to PD1 blocking antibodies were preferentially seen in patients with tumors expressing PDL1.

Figure 21:
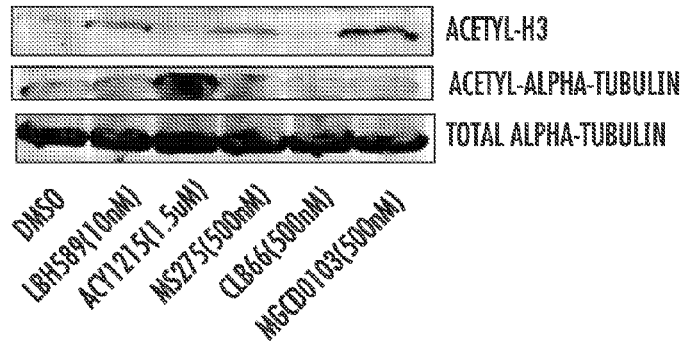
FIG. 21 shows selectivity of HDAC inhibitors. The murine melanoma cell line B16 was treated with indicated HDACi at indicated doses for 24 hours. Cells were lysed and analyzed for acetylated histone 3, acetylated alpha-tubulin and total alpha tubulin protein.
Figure 22:
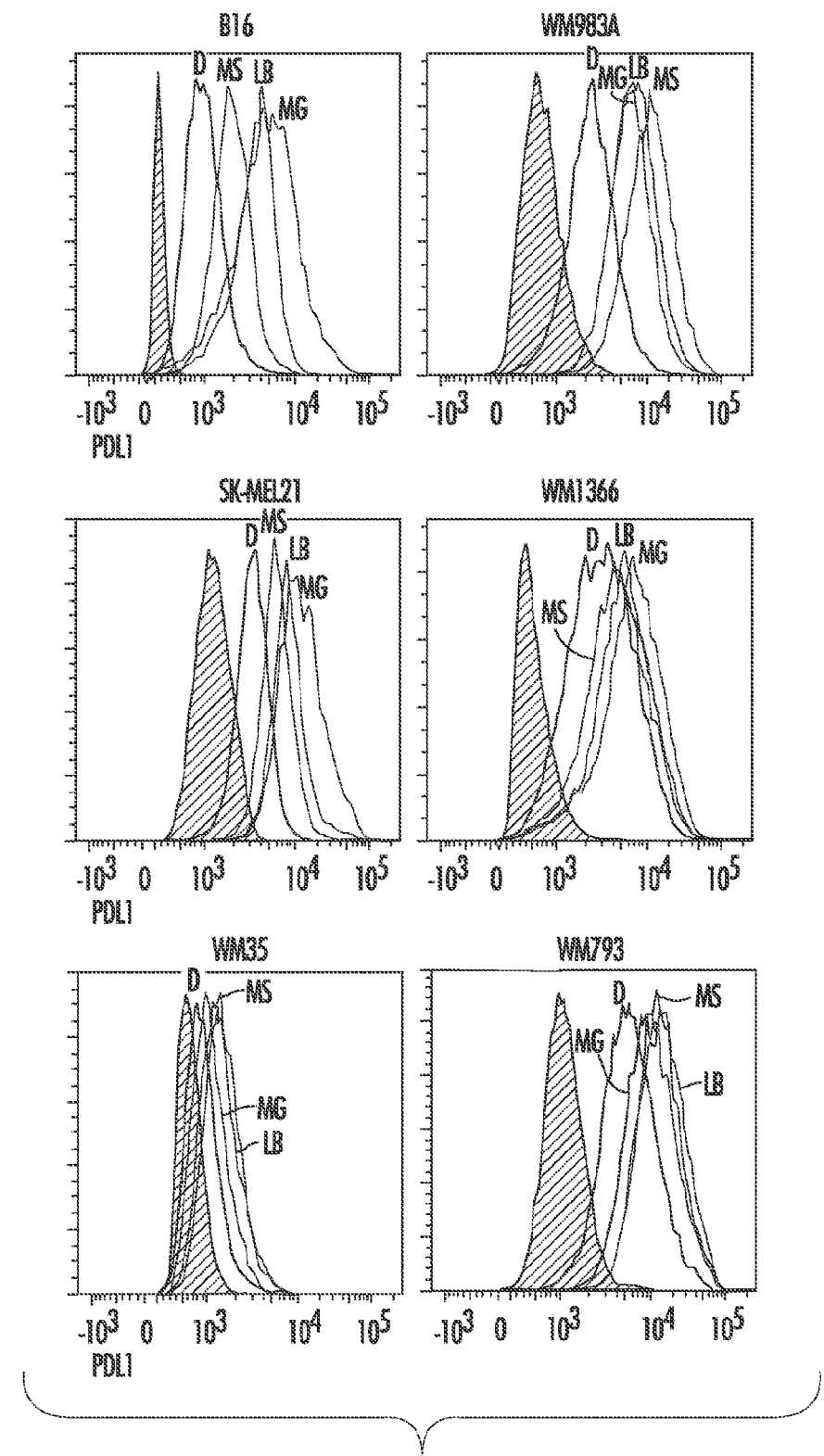
FIG. 22 shows HDAC inhibitors with potency against class I HDACs upregulate PDL1 expression in vitro. B16, WM983A, Sk-Me121, WM1366, WM35, and WM793 melanoma cells lines were treated with DMSO ("D"), 10 nM LBH589 ("LB"), 500 nM MGCD0103 ("MG"), or 500 nM MS275 ("MS") for 72 hours. PDL1 expression was assessed by flow cytometry. Histograms shown are for PDL1 expression or autofluorescence (solid grey) of 10,000 cells or more.
Figure 23:
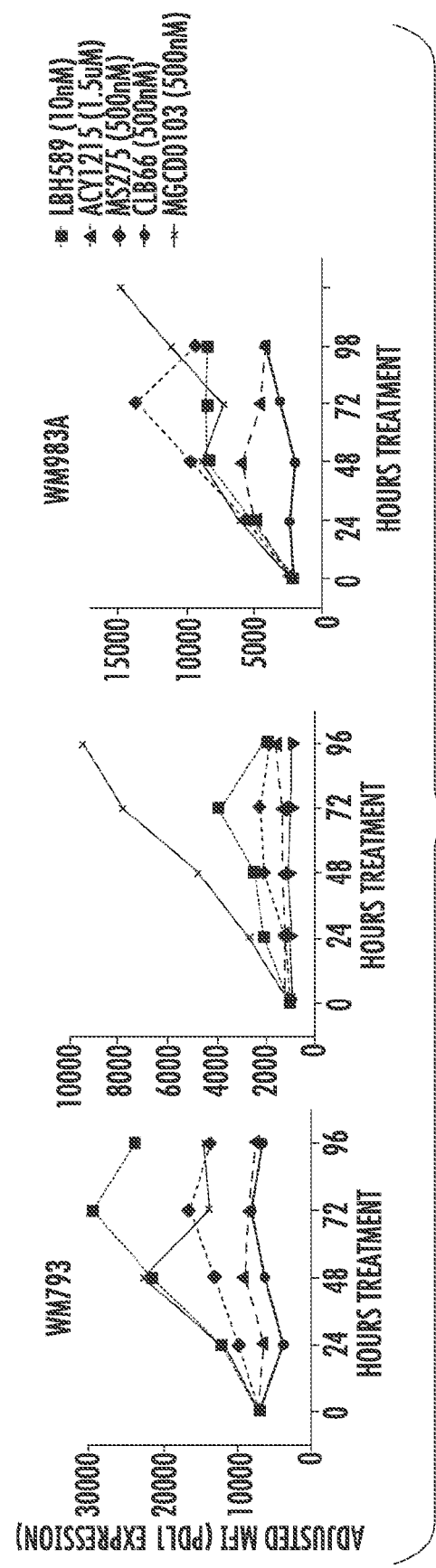
FIG. 23 shows PDL1 upregulation by HDAC inhibitors is long lasting. Melanoma cell lines were treated with DMSO, 10 nM LBH589 (squares), 1.5 µM ACY1215 (triangles), 500 nM MS275 (diamonds), 500 nM CLB66 (circles), or 500 nM MGCD0103 (X). PDL1 expression at indicated time points was assessed by flow cytometry. Voltages between time point measurements was standardized using rainbow beads with standard emissions. Mean fluorescence intensity minus autofluorescencee is graphed for each time point. DMSO treatment was plotted as zero hours.
Figure 24:
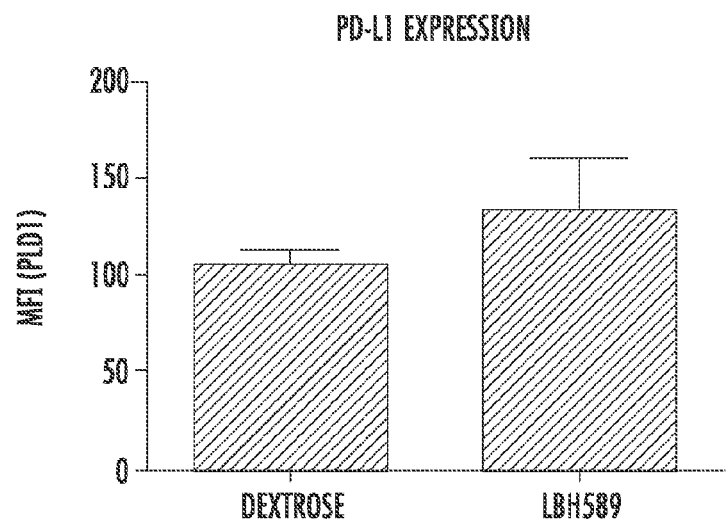
FIG. 24 shows LBH589 upregulates PDL1 expression in vivo. C57BL/6 mice were injected subcutaneously with 100,000 B16 cells. When tumors became palpable, treatment with 15 mg/kg LBH589 via IP injection began on a Mon, Wed, Fri schedule. After one week of treatment, mice were sacrificed, tumors harvest and analyzed by flow cytometry for PDL1 expression.

In this Example, HDACi targeting class I HDACs, but not class II, is shown to augment expression of PDL1 in melanoma cells. Two murine and five human melanoma cell lines were treated for up to 72 hours with DMSO, LBH589 (pan-HDACi), MS275 (class I inhibitor), MGCD0103 (class I inhibitor), an HDAC6 specific inhibitor, or a class IIa inhibitor (FIG. 21). Using flow cytometry, dose dependent, increases in PDL1 expression were found in the LBH589, MS275 and MGCD0103 treated groups, but not in those receiving HDAC6i or class IIa inhibitor, relative to DMSO (FIG. 22). Increased expression was noted as early as 24 hours after treatment and peaked at 72 to 96 hours post-treatment (FIG. 23).

Figure 25:
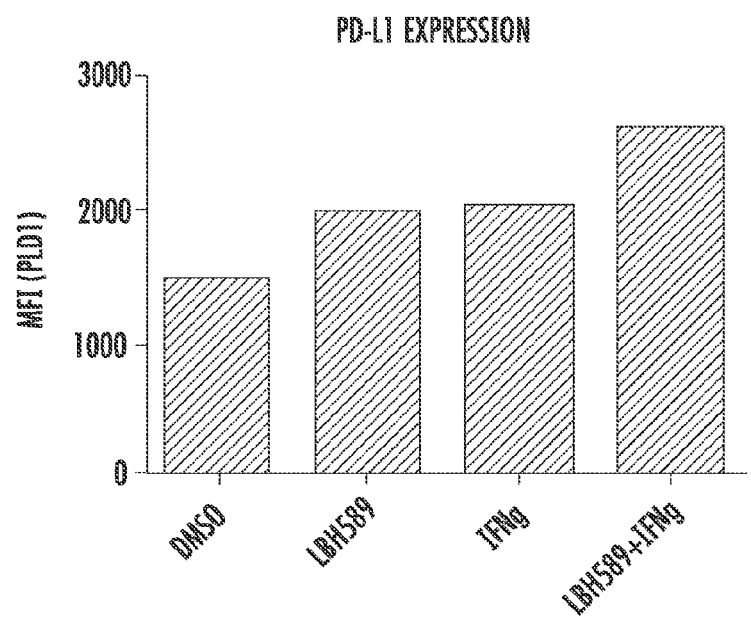
FIG. 25 shows HDAC inhibitor-induced PDL1 expression is enhanced by IFN-γ exposure. SKMe121 cells were treated for 72 hours with DMSO, 10 nM LBH589, 10 ng/mL IFN-γ, or LBH589 and IFN-γ. PDL1 expression was assessed by flow cytometry.
Figure 26:
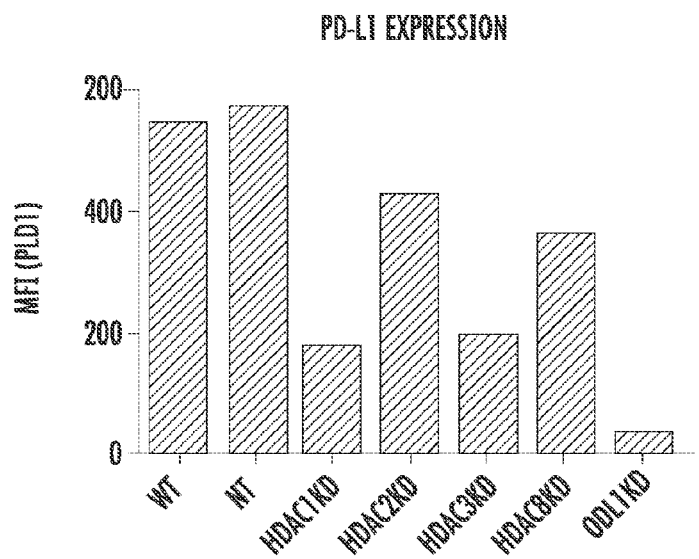
FIG. 26 shows knockdowns of individual HDACs does not recapitulate the enhanced PDL1 expression seen in HDAC inhibitor treated melanoma. Single HDAC knockdowns of class I HDACs were generated as well as a NT control in the melanoma cell line SKMe121. Cells were assessed by flow cytometry for PDL1 expression.
Figure 27:
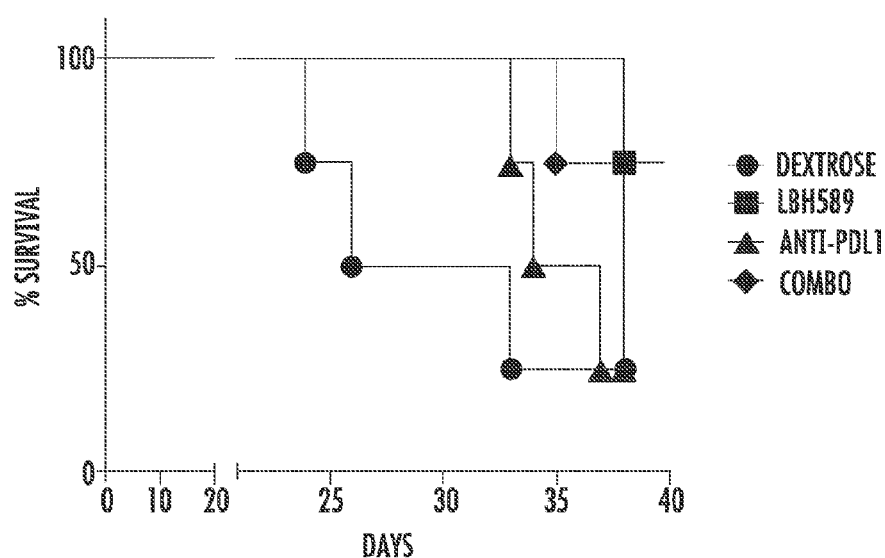
FIG. 27 shows combining LBH589 with PDL1 blockade can enhance survival. C57BL/6 mice were injected subcutaneously with 100,000 B16 cells. On day 10, they were treated with 15 mg/kg LBH589 three times weekly, anti-PDL1 twice weekly, combination of LBH589 and anti-PDL1, or dextrose control injections. Treatment continued for three weeks and mice were monitored for survival.

As IFN-γ is known to upregulate the expression of PDL1 in both normal and transformed cells, experiments were conducted to determine whether these results were associated with induction of IFN-γ expression by the melanoma cells. However, no detectable levels of IFN-γ were seen in either nontreated, class I HDACi, or class II HDACi-treated cells. Melanoma cells treated with HDACi in addition to IFN-γ have enhanced expression of PDL1 relative to either treatment alone (FIG. 25). To further gain insight into the specific HDAC regulating the expression of PDL1, experiments utilizing knockdowns (KD) of individual class I HDACs were performed. In all KD melanoma cells no increase in PDL1 expression was seen (FIG. 26), suggesting that the increased expression of PDL1 is dependent on inhibition of multiple class I HDACs. Supporting this conclusion, treatment of class I HDAC-KDs with HDACi recapitulates the increased PDL1 expression seen with WT melanoma. Finally, in in vivo experiments combining treatment of melanoma bearing mice with anti-PDL1 antibodies, mice receiving the combination treatment had a survival advantage over those receiving PDL1 blocking antibodies or HDACi alone (FIG. 27). These results provide a strong rationale for the evaluation of combination therapies utilizing PDL1 or PD1 blocking antibodies in combination with HDACi.

These results demonstrated that HDAC inhibitors with potency against class I HDACs upregulate the expression of PDL1 in melanoma cell lines. This upregulation occurs in vitro and in vivo, and is long lasting. Evaluation of IFN-γ as a mechanism of PDL1 upregualtion reveals that PDL1 upregulation is further increased by the addition of exogneous IFN-γ. Additionally, HDACi treated melanomas fail to produce IFN-γ, TNF or TGF-b, highlighting other cytokines or an alternative mechanism of PDL1 upregulation. Furthermore, data utilizing knock down of individual class I HDACs does not recapitulate the PDL1 upregulation seen by HDACi. This may indicate that PDL1 upregulation is dependent on inhibition of a combination of class I HDACs. Finally, in vivo experiments show promising results with a combination of the HDACi LBH589 and anti-PDL1 blockade.

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

What is claimed is:

1. A method for treating a melanoma in a subject, comprising administering to the subject a thereapeutically effective amount of a histone deacetylase (HDAC) inhibitor and a thereapeutically effective amount of a Program Death Receptor Ligand 1 (PDL1) inhibitor, a Programmed Death 1 receptor (PD1) inhibitor, or a combination thereof.

2. The method of claim 1, wherein the HDAC inhibitor is a class I HDAC inhibitor.

3. The method of claim 2, wherein the tumor comprises low PDL1 expression.

4. The method of claim 1, wherein the HDAC inhibitor is a selective HDAC6 inhibitor.

5. The method of claim 4, wherein the selective HDAC6 inhibitor is selected from the group consisting of ACY-1215, Tubacin, Tubastatin A, ST-3-06, and ST-2-92.

* * * * *